US011538569B2

(12) United States Patent
Mace et al.

(10) Patent No.: US 11,538,569 B2
(45) Date of Patent: Dec. 27, 2022

(54) METHODS AND SYSTEMS FOR QUANTITATIVE COLORIMETRIC CAPNOMETRY

(71) Applicant: FREESPIRA, INC., Kirkland, WA (US)

(72) Inventors: Leslie E. Mace, Bend, OR (US); Elizabeth K. Siegelman, Palo Alto, CA (US); Debra L. Reisenthel, Pleasanton, CA (US); Simon W. H. Thomas, Danville, CA (US)

(73) Assignee: Freespira. Inc., Kirkland, WA (US)

( * ) Notice: Subject to any disclaimer, the term of this patent is extended or adjusted under 35 U.S.C. 154(b) by 735 days.

(21) Appl. No.: 16/050,340

(22) Filed: Jul. 31, 2018

(65) Prior Publication Data

US 2018/0335440 A1 Nov. 22, 2018

Related U.S. Application Data

(62) Division of application No. 14/902,075, filed as application No. PCT/US2014/046803 on Jul. 16, 2014, now Pat. No. 10,175,254.

(Continued)

(51) Int. Cl.
*G01N 21/78* (2006.01)
*A61B 5/08* (2006.01)
(Continued)

(52) U.S. Cl.
CPC ........... *G16H 20/30* (2018.01); *A61B 5/0075* (2013.01); *A61B 5/082* (2013.01); *A61B 5/0816* (2013.01);
(Continued)

(58) Field of Classification Search
CPC ........ G16H 20/30; G16H 20/70; G16H 40/40; A61B 5/7415; A61B 5/742–745;
(Continued)

(56) References Cited

U.S. PATENT DOCUMENTS 3,723,062 A 3/1973 Dahms
3,754,867 A 8/1973 Guenther
(Continued)

FOREIGN PATENT DOCUMENTS

EP 1965198 A1 9/2008
WO WO89/07957 A1 9/1989
(Continued)

OTHER PUBLICATIONS

Andersson et al.; Camera-Based Colour Contrast Evaluation; SP; 23 pgs.; 2012 (This paper/report known to applicant(s) at least as of Nov. 2013).
(Continued)

*Primary Examiner* — Catherine B Kuhlman
(74) *Attorney, Agent, or Firm* — Shay Glenn LLP

(57) ABSTRACT

Quantitative colorimetric carbon dioxide detection and measurement systems are disclosed. The systems can include a gas conduit, a colorimetric indicator adapted to exhibit a color change in response to exposure to carbon dioxide gas, a temperature controller operatively coupled to the colorimetric indicator and configured to control the temperature of the colorimetric indicator, an electro-optical sensor assembly including a light source or sources adapted to transmit light to the colorimetric indicator, and a photodiode or photodiodes configured to detect light reflected from the colorimetric indicator and to generate a measurement signal, and a processor in communication with the electro-optical sensor assembly. The processor can be configured to receive the measurement signal generated by the electro-optical sensor assembly and to compute a concentration of carbon dioxide based on the measurement signal. Methods for using the systems are also disclosed including providing a breathing therapy to a patient or user.

9 Claims, 17 Drawing Sheets

Related U.S. Application Data

(60) Provisional application No. 61/846,742, filed on Jul. 16, 2013.

(51) Int. Cl.

| | | |
|---|---|---|
| *G01N 21/31* | (2006.01) | |
| *A61B 5/097* | (2006.01) | |
| *G16H 20/30* | (2018.01) | |
| *A61B 5/00* | (2006.01) | |
| *A61B 5/103* | (2006.01) | |
| *A61B 5/083* | (2006.01) | |
| *G16H 40/63* | (2018.01) | |
| *G16H 40/67* | (2018.01) | |
| *G16H 40/40* | (2018.01) | |
| *G16H 50/20* | (2018.01) | |
| *G16H 20/40* | (2018.01) | |
| *G01N 33/84* | (2006.01) | |
| *A61M 16/00* | (2006.01) | |
| *H04M 1/72412* | (2021.01) | |
| *G01N 21/77* | (2006.01) | |

(52) U.S. Cl.
CPC .......... *A61B 5/0836* (2013.01); *A61B 5/1032* (2013.01); *A61B 5/486* (2013.01); *A61B 5/7415* (2013.01); *G01N 21/78* (2013.01); *G01N 21/783* (2013.01); *G01N 33/84* (2013.01); *G16H 20/40* (2018.01); *G16H 40/40* (2018.01); *G16H 40/63* (2018.01); *G16H 40/67* (2018.01); *G16H 50/20* (2018.01); *A61B 5/097* (2013.01); *A61B 5/4836* (2013.01); *A61B 2560/0223* (2013.01); *A61M 16/0051* (2013.01); *A61M 16/024* (2017.08); *A61M 2205/3303* (2013.01); *A61M 2205/581* (2013.01); *A61M 2205/582* (2013.01); *A61M 2230/432* (2013.01); *G01N 21/3151* (2013.01); *G01N 2021/7773* (2013.01); *G01N 2201/0231* (2013.01); *G01N 2201/062* (2013.01); *G01N 2201/1211* (2013.01); *H04M 1/72412* (2021.01)

(58) Field of Classification Search
CPC ....... A61B 5/486; A61B 5/082; A61B 5/0836; A61B 5/1032; A61B 5/097; A61M 2230/432; A61M 2021/0005–0088; A61M 21/00–02

See application file for complete search history.

(56) References Cited

U.S. PATENT DOCUMENTS

| | | | |
|---|---|---|---|
| 4,421,719 A | 12/1983 | Burleigh | |
| 4,580,574 A | 4/1986 | Gavish | |
| 4,879,999 A | 11/1989 | Leiman et al. | |
| 4,921,642 A | 5/1990 | LaTorraca | |
| 5,037,615 A | 8/1991 | Kane | |
| 5,047,208 A | 9/1991 | Schweitzer et al. | |
| 5,071,526 A | 12/1991 | Pletcher et al. | |
| 5,076,281 A | 12/1991 | Gavish | |
| 5,095,900 A | 3/1992 | Fertig et al. | |
| 5,096,671 A | 3/1992 | Kane et al. | |
| 5,124,130 A | 6/1992 | Costello et al. | |
| 5,181,082 A | 1/1993 | Jeannotte et al. | |
| 5,273,029 A | 12/1993 | Wilk et al. | |
| 5,423,328 A | 6/1995 | Gavish | |
| 5,468,451 A | 11/1995 | Gedeon | |
| 5,529,841 A | 6/1996 | Neihof | |
| 5,583,282 A | 12/1996 | Tom | |
| 5,618,495 A | 4/1997 | Mount et al. | |
| 5,749,358 A | 5/1998 | Good et al. | |
| 5,788,832 A | 8/1998 | Howard et al. | |
| 5,800,337 A | 9/1998 | Gavish | |
| 5,846,836 A | 12/1998 | Mallow | |
| 5,858,769 A | 1/1999 | DiGuiseppi et al. | |
| 5,937,852 A | 8/1999 | Butler et al. | |
| 6,090,037 A | 7/2000 | Gavish | |
| 6,151,107 A | 11/2000 | Schollermann et al. | |
| 6,174,289 B1 | 1/2001 | Binder | |
| 6,266,998 B1 | 7/2001 | Hackenberg | |
| 6,374,084 B1 | 4/2002 | Fok | |
| 6,428,748 B1 | 8/2002 | Wallach | |
| 6,436,347 B1 | 8/2002 | Gedeon | |
| 6,479,019 B1 | 11/2002 | Goldstein et al. | |
| 6,502,573 B1 | 1/2003 | Ratner | |
| 6,584,974 B1 | 7/2003 | Ratner | |
| 6,662,032 B1 | 12/2003 | Gavish et al. | |
| 6,677,159 B1 | 1/2004 | Mallow | |
| 6,858,182 B1 | 2/2005 | Ito et al. | |
| 6,929,008 B2 | 8/2005 | Geist | |
| 7,014,612 B2 | 3/2006 | Hubbard et al. | |
| 7,017,578 B2 | 3/2006 | Tresnak et al. | |
| 7,026,165 B2 | 4/2006 | DeGrandpre | |
| 7,052,839 B2 | 5/2006 | Nelson et al. | |
| 7,140,370 B2 | 11/2006 | Tresnak et al. | |
| 7,246,622 B2 | 7/2007 | Geist | |
| 7,449,146 B2 | 11/2008 | Rakow et al. | |
| 7,497,821 B2 | 3/2009 | Elliott | |
| 7,578,971 B2 | 8/2009 | Ratner et al. | |
| 7,713,212 B2 | 5/2010 | Elliott | |
| 7,740,904 B2 | 6/2010 | Shahriari | |
| 7,767,143 B2 | 8/2010 | Wendland et al. | |
| 7,811,433 B2 | 10/2010 | Manoukian et al. | |
| 7,850,619 B2 | 12/2010 | Gavish et al. | |
| 7,900,626 B2 | 3/2011 | Daly | |
| 8,256,414 B2 | 9/2012 | Ratner | |
| 8,396,524 B2 | 3/2013 | Ostrowski | |
| 8,420,405 B2 | 4/2013 | Ostrowski et al. | |
| 8,431,087 B2 | 4/2013 | Ostrowski et al. | |
| 8,431,088 B2 | 4/2013 | Ostrowski et al. | |
| 8,449,834 B2 | 5/2013 | Ostrowski et al. | |
| 2001/0004909 A1 | 6/2001 | Pope et al. | |
| 2002/0024888 A1 | 2/2002 | Schreiber | |
| 2002/0026937 A1* | 3/2002 | Mault | A61B 5/0537 128/200.24 |
| 2002/0031447 A1 | 3/2002 | Brinz et al. | |
| 2003/0047188 A1 | 3/2003 | Mace et al. | |
| 2003/0225324 A1* | 12/2003 | Anderson | A61B 5/6885 600/364 |
| 2004/0062682 A1 | 4/2004 | Rakow et al. | |
| 2004/0116784 A1* | 6/2004 | Gavish | A61B 5/14551 600/300 |
| 2006/0008919 A1 | 1/2006 | Boay et al. | |
| 2006/0047202 A1 | 3/2006 | Elliott | |
| 2006/0102171 A1 | 5/2006 | Gavish | |
| 2006/0219876 A1 | 10/2006 | Halter | |
| 2006/0257094 A1 | 11/2006 | McEvoy et al. | |
| 2007/0081162 A1 | 4/2007 | Roller et al. | |
| 2007/0225612 A1 | 9/2007 | Mace et al. | |
| 2008/0077036 A1 | 3/2008 | Baker et al. | |
| 2008/0138890 A1 | 6/2008 | Horiike et al. | |
| 2009/0018631 A1 | 1/2009 | Snoderly | |
| 2009/0095290 A1 | 4/2009 | Cain et al. | |
| 2009/0165801 A1 | 7/2009 | Ostrowski | |
| 2010/0065063 A1 | 3/2010 | Pagan | |
| 2010/0178203 A1 | 7/2010 | Kane et al. | |
| 2010/0292549 A1 | 11/2010 | Shuler | |
| 2010/0298899 A1 | 11/2010 | Donnelly et al. | |
| 2010/0310425 A1 | 12/2010 | Piper | |
| 2010/0330703 A1 | 12/2010 | Bernstein et al. | |
| 2011/0046434 A1* | 2/2011 | Schmeink | A61B 5/0816 600/27 |
| 2011/0124115 A1 | 5/2011 | Piper | |
| 2011/0146382 A1 | 6/2011 | Fleischer et al. | |
| 2011/0195491 A1 | 8/2011 | Selinfreund et al. | |
| 2011/0298844 A1 | 12/2011 | Butler et al. | |
| 2012/0021455 A1 | 1/2012 | Clay | |
| 2012/0123287 A1 | 5/2012 | Gedeon | |
| 2012/0179006 A1 | 7/2012 | Jansen et al. | |
| 2012/0215125 A1 | 8/2012 | Orr et al. | |

(56) References Cited

U.S. PATENT DOCUMENTS

| | | | |
|---|---|---|---|
| 2012/0302910 A1* | 11/2012 | Freeman | A61M 16/0084 600/538 |
| 2013/0089839 A1 | 4/2013 | Drane et al. | |
| 2013/0089840 A1 | 4/2013 | Drane et al. | |
| 2013/0089851 A1 | 4/2013 | Drane et al. | |
| 2013/0150746 A1 | 6/2013 | Tao et al. | |
| 2013/0236980 A1* | 9/2013 | Moretti | G01N 21/783 436/133 |
| 2013/0259749 A1 | 10/2013 | Moretti et al. | |
| 2013/0261487 A1 | 10/2013 | Baker et al. | |
| 2014/0276171 A1 | 9/2014 | Hestness et al. | |
| 2016/0245830 A1 | 8/2016 | Mace et al. | |

FOREIGN PATENT DOCUMENTS

| | | | |
|---|---|---|---|
| WO | WO91/16618 A1 | 10/1991 | |
| WO | WO93/14399 A1 | 7/1993 | |
| WO | WO94/10553 A1 | 5/1994 | |
| WO | WO94/22686 A1 | 10/1994 | |
| WO | WO95/03537 A1 | 2/1995 | |
| WO | WO96/24054 A1 | 8/1996 | |
| WO | WO96/24055 A1 | 8/1996 | |
| WO | WO97/10497 A1 | 3/1997 | |
| WO | WO97/14464 A1 | 4/1997 | |
| WO | WO97/33641 A1 | 9/1997 | |
| WO | WO00/02844 A1 | 1/2000 | |
| WO | WO00/02845 A1 | 1/2000 | |
| WO | WO01/04624 A1 | 1/2001 | |
| WO | WO2005/111588 A1 | 11/2005 | |
| WO | WO2005/116239 A2 | 12/2005 | |
| WO | WO2006/023652 A1 | 3/2006 | |
| WO | WO2007/050051 A2 | 5/2007 | |
| WO | WO2008/039423 A2 | 4/2008 | |
| WO | WO2008/062316 A2 | 5/2008 | |
| WO | WO2010/028057 A1 | 3/2010 | |
| WO | WO2010/151329 A1 | 12/2010 | |
| WO | WO2012/114262 A1 | 8/2012 | |
| WO | WO2013/019843 A2 | 2/2013 | |
| WO | WO2015/030648 A1 | 3/2015 | |

OTHER PUBLICATIONS

Bultzingslowen; Development of optical sensors("Optodes") for carbon dioxide and their application to modified atmosphere packaging (MAP); (dissertation); Univ. of Regensburg; pp. 13, 20, 38, 87 and 88; submitted: May 2003; published: Apr. 2004.

Gedeon et al.; A new colorimetric breath indicator (Colibri); Anesthesia; 49 (9); pp. 798-803; Sep. 1994.

Johansen et al.; Normalizing CO2 in chronic hyperventilation by means of a novel breathing mask: a pilot study; Clin Respir J.; 7(4); pp. 359-366; Oct. 2013.

Kolb, Peter; BUTEYKO: Guide for Doctors; Rev. 1.1; 16 pgs.; Oct. 2001 (http://buteyko.ie/images/pdf/Buteyko_Guide_for_doctors.pdf).

Kuutmann et al.; Smartphone Capnography: evaluation of the concept and the associated CO2 indicating sensor (thesis); KTH STH Royal Institute of Technology (Sweden); 114 pgs.; (year of pub. earlier than effective US filing date and any foreign priority date) 2014.

Meuret et al.; Feedback of end-tidal pCO2 as a therapeutic approach for panic disorder; Journal of Psychiatric Research; 42(7); pp. 560-568; Jun. 2008.

Meuret et al.; Respiratory and Cognitive Mediators of Treatment Change in Panic Disorder: Evidence for Intervention Specificity; J Consult Clin Psychol.; 78(5); pp. 691-704; Oct. 2010.

Meuret et al.; Respiratory biofeedback-assisted therapy in panic disorder; Behavior Modification; 25(4); pp. 584-605; Sep. 2001.

Meuret et al.; Targeting pCO2 in Asthma: Pilot Evaluation of a Capnometry-Assisted Breathing Training; App. Physhophysiol Biofeedback; 32(2); pp. 99-109; Jun. 2007.

Mills; Optical sensors for carbon dioxide and their applications; Sensors for Enviroment, Health and Security; M.I. Baraton (ed.); Springer Science and Business Media B.V.; pp. 347-370; Jan. 1, 2009.

Schein et al.; Treating hypertension with a device that slows and regularises breathing: a randomised, double-blind controlled study; J Hum Hypertens.; 15(4); pp. 271-278; Apr. 2001.

Zhao et al.; A Novel Real-time Carbon Dioxide Analyzer for Health and Environmental Applications; Sens Actuators B Chem; 195; pp. 171-176; May 2014.

Zhao et al.; A personal device for analyzing carbon dioxide in real time and real breath: Experimental investigation and computational stimulation; Sensors and Actuators B: Chemical; 183; pp. 627-635; Jul. 5, 2013.

Graham et al.; U.S. Appl. No. 15/578,722 entitled "Devices and methods for calibrating a colorimetric sensor," filed Dec. 1, 2017.

Mills et al.; Breath-by-breath measurement of carbon dioxide using a plastic film optical sensor; Sensors and Actuators B; 39 (1-3); pp. 419-425; Mar. 1997.

Jahnke; Operators guide to eliminating bias in CEM systems; 122 pages retrieved from the internet (https://19january2017snapshot.epa.gov/sites/production/files/2015-05/documents/an_operators_guide_to_eliminating_bias_in_cem_systems.pdf); on May 29, 2020.

* cited by examiner

METHODS AND SYSTEMS FOR QUANTITATIVE COLORIMETRIC CAPNOMETRY

CROSS REFERENCE TO RELATED APPLICATIONS

This application is a divisional application of U.S. application Ser. No. 14/902,075, filed Dec. 30, 2015, which is a 35 U.S.C. § 371 national phase application of International Application No. PCT/US2014/046803, filed Jul. 16, 2014, which claims the benefit under 35 U.S.C. § 119 of U.S. Provisional Patent Application No. 61/846,742, filed Jul. 16, 2013, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments described relate generally to quantitative colorimetric capnometry methods and systems.

BACKGROUND

Methods and devices for measuring quantitative airway carbon dioxide ($CO_2$) gas exchange concentrations and respiratory rate of a subject's breath (capnometry) are well known in the clinical markets. In fact, the use of capnometry during intubated surgical and otherwise critical ventilated patient situations is mandated by standards organizations because it is critical in maintaining safety. By far the most common technology used in commercial instruments is IR spectroscopy because of its accuracy, precision, speed of response and reliability. Infrared absorption spectroscopy capnometers quantify the subject's airway $CO_2$ gas exchange in real time without any airway perturbation or violation of sterility. Unfortunately, this utility requires substantial technological complexity and a high price when compared with other common medical parameter measurements such as temperature, blood pressure, ECG, heart rate and pulse oximetry. Now that the use of capnometry has expanded outside the in-hospital environment to pre-hospital emergency care including non-intubated subject monitoring applications such as dentistry, pain management, conscious sedation, in-home use, etc., there is an increased awareness of the need for less expensive capnometry instruments.

There are many other techniques for measuring gas exchange in a subject's breath. Among these include mass spectrometry, Raman scattering, photoacoustic, piezoelectric, paramagnetic and chemical based instruments. All of these techniques have specific tradeoffs with respect to their complexity, performance and cost. In examining the aspects of these tradeoffs, one technique stands alone as having potential for simplicity, meeting adequate performance criteria at considerably lower cost than other methods; the chemical based colorimetric technique.

Chemical based colorimetric techniques have been utilized in many other applications including qualitative human breath $CO_2$ measurement. However, one of the challenges in using colorimetric techniques is its ability to achieve sufficient response time to capture rapidly changing $CO_2$ concentrations such as is found in a subject's ventilation pattern. Commercially available airway colorimetric products first appeared in the late 1980's, but could only give relative qualitative indications of $CO_2$ concentrations due to their slow response. In the 1990's, improvements to the indicator chemistry formulations were made to enhance the speed of response to breath-by-breath gas concentration variations. For example, in 1994 Dr. Andras Gedeon published test results of a colorimetric indicator compared with an IR spectroscopy based capnometer showing significant similar breath-by-breath response. Details regarding these test results are described in the paper "A New Colorimetric Breath Indicator (Colibri)" published in Anaethesia (1994) volume 49, pages 798-803, which is herein incorporated by reference in its entirety. Since then, Dr. Gedeon and others have also developed and manufactured qualitative colorimetric indicators primarily for use with intubation verification.

Although much has been done to improve chemical based colorimetric techniques, there remains a need for a low cost quantitative $CO_2$ device that provides fast and accurate continuous measurement of a subject's breath-by-breath $CO_2$ levels. Moreover, there is a need for a portable device that can be used by patients at home or otherwise to monitor $CO_2$ levels as part of a treatment protocol. As such, the embodiments described herein provide devices, systems, and methods for addressing at least these concerns. For example, some embodiments provide for electro-optical techniques instead of visual interpretation to detect the color change from $CO_2$ concentrations. Other embodiments provide for devices or systems that display continuous calibrated $CO_2$ concentrations and respiratory rates using colorimetric indicator chemistry. Additionally, methods and devices contemplated herein include new techniques for user calibration and unique patient attachments or patient interface for various clinical applications to allow quantitative monitoring of a spontaneously breathing (non-intubated) subject with a completely robust, portable, very low cost, low power instrument. The simplicity of this instrument is suited, at least, for the technology-unsophisticated, home-based user.

In addition, some embodiments described provide examples of breathing therapy for treating any number of disorders including panic disorder, hypertension, post-traumatic stress disorder (PTSD), asthma etc. Although breathing therapies or methods (e.g. yoga and meditation) have been used in the past as ways to reduce anxiety or hyperventilation, such breathing techniques are focused primarily on relaxing or calming the practitioner and not on modifying carbon dioxide levels during respiration for treatment. In particular, previous techniques have not used a quantitative colorimetric carbon dioxide system for therapy. As such, the quantitative colorimetric devices and systems described herein can be used to provide breathing therapy treatment by, for example, helping patients modify end-tidal $CO_2$ levels to help treat panic disorder, PTSD, anxiety, general anxiety disorder, obsessive-compulsive disorder, social phobia, depression, apnea, migraines, epilepsy, asthma, hypertension, conscious sedation, emergency medical services (EMS), etc.

SUMMARY OF THE DISCLOSURE

The present disclosure relates to quantitative colorimetric systems and methods for using the same. The quantitative colorimetric systems can be used to provide a user with a breathing therapy.

In general, in some embodiments, quantitative colorimetric carbon dioxide detection and measurement systems include: a gas conduit, a colorimetric indicator adapted to exhibit a color change in response to exposure to carbon dioxide gas, a temperature controller operatively coupled to the colorimetric indicator and configured to control the temperature of the colorimetric indicator, an electro-optical sensor assembly includes a light source or sources adapted to transmit light to the colorimetric indicator, and a photodiode or photodiodes configured to detect light reflected from the colorimetric indicator and to generate a measurement signal, and a processor in communication with the electro-optical sensor assembly. The processor is configured to receive the measurement signal generated by the electro-optical sensor assembly.

This and other embodiments can include one or more of the following features. The processer can be further configured to compute a concentration of carbon dioxide based on the measurement signal. The processor can be within a housing of the quantitative colorimetric carbon dioxide detection and measurement system. The system can further include a mobile display device, wherein the processor can be further configured to transmit the measurement signal to the mobile device and the mobile device is configured to compute a concentration of the carbon dioxide and a respiration rate based on the measurement signal. The system can further include a display device, wherein the processor can be configured to transmit the computed concentration of carbon dioxide to the display device and the display device is configured to display the computed concentration of carbon dioxide. The processor can be configured to control the temperature controller to maintain the colorimetric indicator at a pre-determined temperature. The pre-determined temperature can be from 20° C. to about 50° C. The system can further include a pump configured to move a sample of gas in the gas conduit into contact with the colorimetric indicator. The gas conduit can include a separate disposable sample inlet tube containing the colorimetric indicator. The disposable sample inlet tube can be configured to removably engage with and couple to the electro-optical sensor assembly. The system can further include a display in communication with the processor. The display can further be configured to display a user interface for operating the system. The system can further include a sensor cable coupling the electro-optical sensor assembly to the processor. The system can be wearable. The system can be configured to continuously measure a user's exhaled air during breathing. The processor can be configured to provide a guided breathing maneuver to thereby alter the amount of carbon dioxide measured from a user's exhaled air. The processor can be configured to provide visual and/or audio cues to guide the user's breathing. The processor can be configured to provide the user a guided breathing maneuver based on the quantity of carbon dioxide measured from the user's exhaled breath. The processor can be configured to provide the user a guided breathing maneuver based on the respiration rate measured from the user's exhaled breath. The system can further include a nasal and/or oral cannula adapted for collecting a sample of a user's exhaled breath for exhaled carbon dioxide measurement. The cannula can be configured to be in fluid communication with the gas conduit. The gas conduit includes a nasal and/or oral cannula adapted for collecting a sample of a user's exhaled breath for exhaled carbon dioxide measurement. The gas conduit can include the colorimetric indicator and nasal and/or oral cannula. The gas conduit, colorimetric indicator, and nasal and/or oral cannula can be configured for a single use. The processor can be configured to measure a respiration rate. The system can further include a device configured to electronically receive the computed $CO_2$ concentration and execute a breathing therapy program that can further include a set of tone patterns adapted for guiding a user's breathing technique while monitoring the user's $CO_2$ levels. The tone patterns can correspond to a total breath time, an inhalation time, an expiration time, a first pause time between inhalation to exhalation, and a second pause time between exhalation and inhalation. The tone patterns can provide silence for the first and second pause times. The device can be configured to record the user's information. The device can be configured to visually display a goal line corresponding to a target end-tidal $CO_2$ level on an end-tidal $CO_2$ graph. The device can be a mobile device. The electro-optical assembly can include one photodiode and two alternating light sources. The electro-optical assembly can include two photodiodes and two light sources. The pump can be upstream of the colorimetric indicator. The pump can be downstream of the colorimetric indicator. The temperature controller can be further configured to control a temperature of the electro-optical sensor. The temperature controller can include a heater. The system can further include a temperature probe configured to measure the temperature of the colorimetric indicator. The processor can be configured to apply a temperature correction to the measurement signal based on the temperature of the colorimetric indicator.

In general, in some embodiments, breathing therapy methods include:

(1) receiving at least a portion of a user's exhaled air in a gas inlet of a quantitative colorimetric detection system;

(2) measuring a user's end-tidal $CO_2$ levels with the quantitative colorimetric detection system based on a color change resulting from exposure of the system to the user's exhaled air; and (3) outputting a set of visual and/or audio cues from the quantitative colorimetric system with instructions for the user to adjust their breathing pattern to coincide with the cues to thereby modify the user's exhaled $CO_2$ levels.

The breathing pattern can include the exhaled $CO_2$ level and respiration rate. The method can further include displaying the user's measured $CO_2$ levels to provide visual feedback during treatment. The method can further include displaying the user's breathing rate to provide visual feedback during treatment. The method can further include the therapy directing the user's end-tidal $CO_2$ levels to a level between about 37 mmHg and 43 mmHg. The outputting step can further include outputting a set of timed tones having an audible sequence of rising tones, falling tones, and silence. The rising tones can indicate respiration, falling tones can indicate expiration, and silence can indicate a pause in the user's respiration. The adjusting step can further include the user breathing in at the rising tones, breathing out at the falling tones and not breathing during silent periods. The method can further include measuring a baseline $CO_2$ level for the user prior to modification. The method can further include treating post-traumatic stress disorder (PTSD), panic disorder, anxiety, asthma, hypertension, obsessive-compulsive disorder, social phobia, depression, apnea, migraines, or epilepsy by training the user to modify their exhaled $CO_2$ levels. The method can further include controlling a temperature of a colorimetric indicator in the quantitative colorimetric detection system while measuring the user's end-tidal $CO_2$ levels. The method can further include measuring a temperature of a colorimetric indicator in the quantitative colorimetric detection system while measuring the user's end-tidal $CO_2$ levels and applying a temperature correction to the measured color change.

In general, in some embodiments, method for treating a user with a panic disorder with a breathing therapy include:

(1) measuring a user's baseline end-tidal $CO_2$ and breathing rate. The user's $CO_2$ is measured with a quantitative colorimetric $CO_2$ detection system;

(2) determining a target end-tidal $CO_2$ level and a target breathing rate for the user; and (3) outputting a set of tone patterns with instructions to modify the user's end-tidal $CO_2$ levels and breathing rate from an audio device during a first time period and discontinuing the output of the set of tone patterns during a second time period. The tone patterns are configured to guide the user's breathing pattern to achieve the target end-tidal $CO_2$ level and target breathing rate.

In some embodiments the first time period can be about ten minutes or less. In some embodiments the second time period can be about five minutes or less. In some embodiments the set of tone patterns can correspond to a target breathing pattern. In some embodiments the target breathing rate can be between about six breaths-per-minute and 13 breaths-per-minute.

In general, in some embodiments, quantitative colorimetric carbon dioxide detection systems include: a colorimetric indicator adapted to change color in response to exposure to a quantity of carbon dioxide gas, a temperature controller coupled to the colorimetric indicator and configured to control a temperature of the colorimetric indicator, an electro-optical sensor assembly coupled to the colorimetric indicator, a photodiode is configured to detect a first reflected light based on the first wavelength and a second reflected light based on the second wavelength and to generate an first electrical signal based on the first reflected light and a second electrical signal based on the second reflected light, and a processor in communication with the electro-optical sensor assembly and temperature controller. The electro-optical sensor assembly includes light sources adapted to transmit a first wavelength and a second wavelength to the colorimetric indicator. The first wavelength is configured to be sensitive to an indicator color change and the second wavelength is configured to not be sensitive to an indicator color change. The processor is configured to receive the electrical signals generated by the electro-optical sensor assembly. The processor utilizes the signals to compute the quantity of carbon dioxide exposed to the indicator.

The electro-optical sensor assembly can be configured to alternately transmit the first and second wavelengths.

In general, in some embodiments, methods of calibrating a quantitative colorimetric carbon dioxide detection system include:

(1) exposing a chemical colorimetric indicator to a reference gas;

(2) transmitting light to a surface of the indicator while the indicator is exposed to the reference gas;

(3) measuring a first color of the indicator based on the exposure to the reference gas;

(4) exposing the indicator to an ambient gas;

(5) measuring a second color of the indicator based on the exposure to the ambient gas;

(6) deriving a "span" calibration based on the difference between the first color of the indicator and the second color of the indicator; and (7) applying the span calibration to a measurement of the color of the indicator exposed to a breath sample.

Exposing the chemical colorimetric indicator to a reference gas can include exposing the indicator to a sealed ampoule filled with a reference sample having a known carbon dioxide concentration. Exposing the indicator to an ambient gas can include removing the seal on the ampoule to allow exposure of the indicator to ambient air.

In general, in one embodiment, a method for quantitatively measuring carbon dioxide, includes:

(1) passing a sample gas through a gas conduit;

(2) contacting a colorimetric indicator with the sample gas. The colorimetric indicator is adapted to exhibit a color change in response to exposure to carbon dioxide gas;

(3) controlling the temperature of the colorimetric indicator with a temperature controller coupled to the colorimetric indicator while contacting the colorimetric indicator with the sample gas;

(4) transmitting light to the colorimetric indicator with an electro-optical sensor assembly comprising a light source or sources while contacting the colorimetric indicator with the sample gas;

(5) detecting light reflected from the colorimetric indicator with a photodiode;

(6) generating a measurement signal from the photodiode based on the reflected light;

(7) sending the measurement signal to a processor; and (8) computing the concentration of carbon dioxide in the sample gas with the processor based on the measurement signal.

Computing the concentration of carbon dioxide with the processor can be based on the color change of the colorimetric indicator. The methods can further include maintaining the colorimetric indicator at a pre-determined temperature with the temperature controller. The pre-determined temperature can be from about 20° C. to about 50° C. The methods can further include moving the sample gas in the gas conduit into contact with the colorimetric indicator using a pump. The methods can further include displaying a user interface for operating the system. The methods can further include continuously measuring a user's exhaled air during breathing. The methods can further include providing a guided breathing maneuver to the user with instructions to alter the amount of carbon dioxide measured from the user's exhaled air. The methods can further include providing visual and/or audio cues to guide the user's breathing. The methods can further include measuring the breathing rate of a user's breathing. The methods can further include electronically sending the computed $CO_2$ concentration to a device and executing a breathing therapy program comprising a set of tone patterns for guiding a user's breathing pattern while monitoring the user's $CO_2$ levels with the device. The device can be a mobile device with a display. The device can include a display. The breathing pattern can include the $CO_2$ levels and respiration rate. The tone patterns can correspond to a total breath time, an inhalation time, an expiration time, a first pause time between inhalation to exhalation, and a second pause time between exhalation and inhalation. The tone patterns can further provide silence for the first and second pause times. The methods can further include recording the user's information with the device. The methods can further include visually displaying on the device a goal line corresponding to a target end-tidal $CO_2$ level on an end-tidal $CO_2$ graph.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Quantitative colorimetric carbon dioxide detection and measurement systems are disclosed herein. The systems can include a gas conduit configured to provide a carbon dioxide gas sample to a colorimetric indicator. The colorimetric indicator is adapted to exhibit a color change in response to exposure to carbon dioxide gas. An electro-optical sensor assembly including a light source or sources can transmit light to the colorimetric indicator. A photodiode or photodiodes can detect light reflected from the colorimetric indicator and generate a measurement signal corresponding to the color change of the colorimetric indicator in response to the exposure to carbon dioxide gas. A processor in communication with the electro-optical sensor assembly can receive the measurement signal generated by the electro-optical sensor assembly and compute a concentration of carbon dioxide based on the measurement signal. Methods for using the systems are also disclosed including providing a breathing therapy to a patient or user.

Reference will now be made in detail to exemplary embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
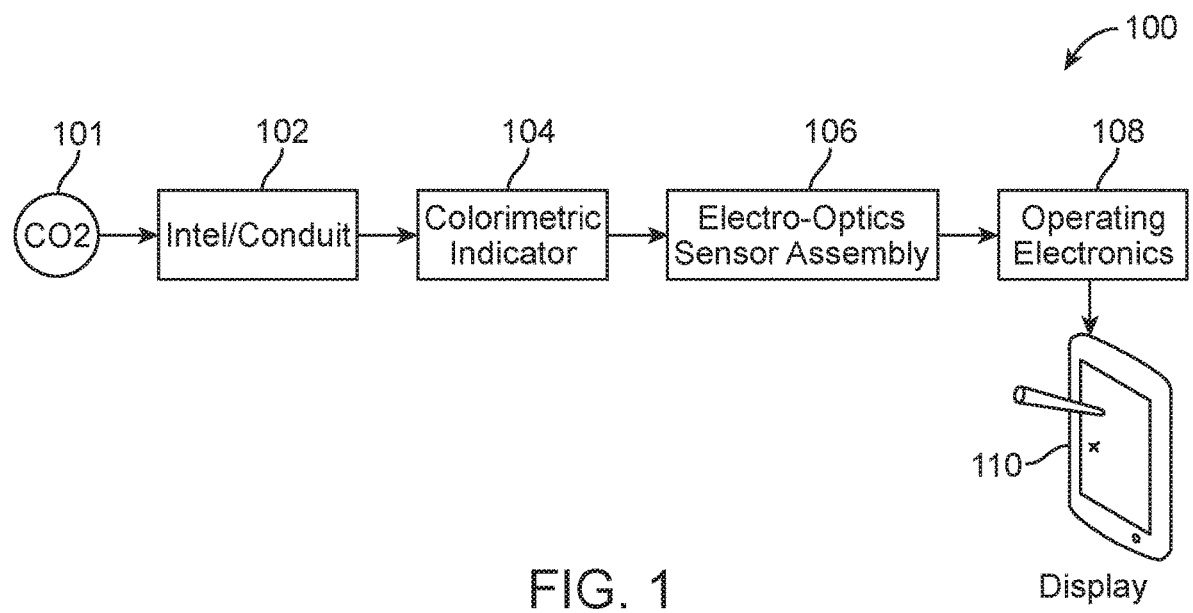
FIG. 1 is a schematic diagram of a quantitative colorimetric carbon dioxide detector system in accordance with some embodiments.

Various embodiments disclosed herein are directed to devices and systems that provide quantitative colorimetric $CO_2$ measurement from a breath sample. FIG. 1 shows an example of a quantitative colorimetric $CO_2$ detection system. The detection system 100 may include an inlet/conduit 102 directing a breath sample or a gas to enter the detection system. In some embodiments, the inlet/conduit 102 may be coupled to or can include a gas or fluid conduit to allow gas to pass from the inlet/conduit 102 to a colorimetric indicator 104. In some embodiments, the inlet/conduit 102 may connect to or be in fluid communication with a sensing chamber having sensing elements, such as a colorimetric indicator and electro-optical assembly.

Once a gas sample, which may be a portion of a patient's exhaled breath or the complete exhaled breath, reaches the colorimetric indicator 104, the colorimetric indicator 104 changes color based on the volume percent concentration of $CO_2$ exposed to the indicator 104. For example, in some embodiments, the colorimetric indicator 104 is blue when less than 0.5% $CO_2$ is present, blue-green when 1% to 2% $CO_2$ is present, green when 2% to 3% $CO_2$ is present and yellow when approximately 5% $CO_2$ is present. The specific colors visually apparent at specific $CO_2$ concentrations levels within the range of approximately 0.5% to 5% can be adjusted with different chemistry formulations.

With quantitative $CO_2$ colorimetric measurements, once the color shift is determined, it can be desirable that the specific color shift at specific $CO_2$ concentrations is repeatable. This may involve manufacturing quality assurance processes to validate this characteristic within various batches of colorimetric material.

In some embodiments, the concentration of carbon dioxide detected by the indicator is used to determine or derive a partial pressure for the carbon dioxide in the gas or breath sample. For example, if a total pressure of a breath sample is known (or measured) and the percentage of carbon dioxide present in that breath sample is measured, then the partial pressure of the carbon dioxide in the sample can be calculated or derived. Additionally, in some cases, calculations are performed to determine a mean, median, or mode gas component value. In some cases, the carbon dioxide values measured in multiple breaths (e.g. more than one exhalation or inhalation) are averaged to determine a computed average carbon dioxide value.

In further embodiments, the indicator is adapted to change color based on the partial pressure of carbon dioxide present. In some cases, the indicator is adapted to change color according to partial pressures of about 7.6 mmHg (first color); 15.2 mmHg (second color); 22.8 mmHg (third color); 30.4 mmHg (fourth color); and 38 mmHg (fifth color) of a gas component such as carbon dioxide.

Several different chemical formulations for colorimetric indicators can be used in the contemplated embodiments. Some embodiments include a chemical colorimetric indicator having a substrate with a reagent that is reactive to $CO_2$. Once the substrate is exposed to the $CO_2$, the reagent reacts to create a color change in the substrate. In some embodiments, the indicator is a thin film or membrane with a $CO_2$ sensitive reagent. In some embodiments, for quantitative measurements, the color shift in the presence of $CO_2$ is indicated on both sides of the film.

Referring again to FIG. 1, the colorimetric indicator may be coupled to an electro-optical sensor assembly 106. The electro-optical sensor assembly may be configured to detect the color change in the colorimetric indicator. For example, the assembly 106 may include a light source/emitter such as a mono, bi or tri-color LED assembly that is combined and pulsed to emit certain wavelengths of light ranging from near infrared to ultraviolet that in turn are transmitted to a surface of the colorimetric indicator. Some of the light that encounters the surface of the indicator will be reflected, scattered, or absorbed by the indicator. Light reflected back from the indicator may be synchronously detected by a photodetector such as one or more photodiodes that generates an electrical signal based on the detected reflected light.

In some embodiments, an indicator color change is detected by determining the intensity and wavelength shift in the light reflected from the indicator. In some cases, a reference light source having one or more reference wavelengths is alternately transmitted to the indicator surface. For example, a light of a first wavelength may be alternated with a light of a second wavelength for transmission to the indicator. The reference wavelength(s) may be selected so as to not be sensitive to the $CO_2$ induced wavelength shift but are sensitive to other factors such as surface contamination, ambient light, optics misalignment, temperature effects and colorimetric indicator aging. A microprocessor can be employed to compare the reference reflected light output with the reflected light output from the $CO_2$ induced signal to compensate for artifact and provide other user error messages. In some cases, the reference wavelength that is not sensitive to the indicator color shift is used to determine measuring conditions (including compensation factors).

Additionally, calibration methods may incorporate a ratiometric, dual wavelength electro-optical measurement system which rejects common mode interferences such as: misalignment of indicator/sensor combination, electro-optical component drift, ambient temperature effects, ambient light effects, indicator contamination (mucus, moisture, dust, air pollution compounds), presence of anesthetic agents or nebulized medications, indicator aging phenomena; batch to batch chemistry variability, etc. Ratiometric measurements that may be suitable include those commonly used with other optically based sensor systems such as IR spectroscopy based capnometers and pulse oximeters.

As described, the electro-optical assembly 106, shown in FIG. 1, may include one or more light emitter(s), one or more photodetector(s), and other suitable components such as a lens, diffuser or collimator. In some embodiments, the photodetector receives the reflected light from the indicator and generates an electrical signal. The electrical signal may be transmitted to a microcontroller or a processor. Depending on the reflected light received by the photodetector, the photodetector may generate one or more electrical signals based on the received reflected light. For example, if a first electric signal may be generated for a first detected reflected light and a second electric signal may be generated for a second detected reflected light. The first and second signals may be used for comparison or computation to measure the tested gas component in the sample. In some embodiments one or more photodetectors can be used with the one or more light emitters. For example, two light emitters could be used with two corresponding photodetectors.

The operating electronics 108 may include a processor configured to receive the electrical signal(s) from the photodetector(s). The processor may be further configured to process the electrical signal and compute the amount of $CO_2$ in the gas sample. The amount of $CO_2$ may be computed in any suitable units including concentration percentage in the breath sample or $CO_2$ partial pressure (mmHg). In some variations, the pressure of the $CO_2$ can be derived from other measured values such as concentration percentage. In Some embodiments the processor is within the housing of the device. In some embodiments the processor is in communication with the system and receives the electrical signal. In some embodiments the processor is external to the quantitative detector.

Additionally, in some embodiments, the processor includes calibration data for the system, which is used to determine the quantity of $CO_2$ based on the color shift detected by the electro-optical assembly 106. In some embodiments a calibration can be applied to the color shift detected by the electro-optical assembly based on a temperature of the colorimetric film or breath sample. The temperature correction or calibration can be a look-up table or formula tailored to the specific colorimetric material. In some embodiments the temperature correction or calibration is applied to the measurement signal by the processor.

In further embodiments, the detection system 100 may include a display or monitor 110. The display 110 may include a user interface for user information input. In other variations, the display 110 may display the computed $CO_2$ measurements. The $CO_2$ measurement values may be in any suitable units including pressure units of Torr or mmHg. In further embodiments, the display 110 may output visual or audio cues guiding the user through a breathing maneuver to modify $CO_2$ levels. In other embodiments the display 110 may be wirelessly connected to the internet including cloud based computational methods. In some embodiments, the display is not a separate component and is instead integrated with the operating electronics 110. For example, the operating electronics and display may be a mobile device such as a smart phone, tablet, or other computing device programmed to interface with and operate one or more of the electro-optical sensor assembly, colorimetric indicator, and inlet. In some embodiments the display is a non-mobile device. For example, the display could be a television or monitor that receives the image data to display. In some embodiments the processor could be attached to or in communication with the television, for example as a gaming system, media streaming device, antenna, or other device configured to provide image data to an input on a display.

Figure 2:
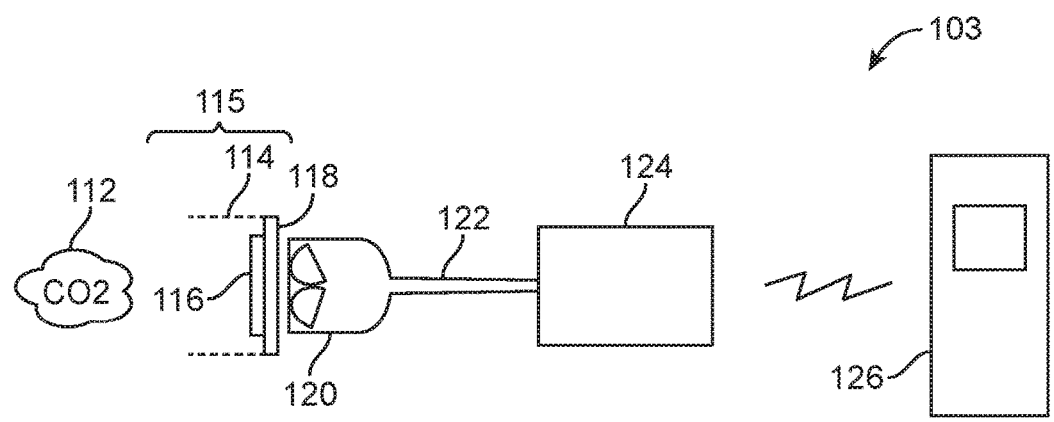
FIG. 2 is a schematic diagram of a quantitative colorimetric carbon dioxide detector system in accordance with some embodiments.

FIG. 2 shows additional details regarding another embodiment of a quantitative colorimetric $CO_2$ detection system 103. The system 103 includes a gas permeable shield or protective shield 114 around a colorimetric chemical indicator 116. In some cases, the shield protects the indicator from physical contamination, such as touching by a user, while allowing fluid (e.g. gas) movement through the shield to the indicator. In some embodiments, an annular ring surrounds and shields the indicator from unwanted contaminating contact. For example, the annular ring may include a cavity in which the indicator sits. The ring may be porous or otherwise gas permeable to allow gas movement to the indicator through the ring.

In some variations, the colorimetric indicator is a thin film or membrane having a reagent that is reactive to $CO_2$. Upon exposure to $CO_2$, the reagent reacts to create a color change. In other embodiments, the color change is indicated on both sides of the thin film or membrane. Advantageously, in some variations, the color change is optically or visually detectable. In some cases, the colorimetric indicator/sensor can be made very small/lightweight (<0.125" diameter) and thus can be placed directly in the exhaled breath flow path. In some embodiments, there is no gas entrainment (vacuum pump) required. As such, colorimetric $CO_2$ sensing can combine the advantages of both sidestream capnometers (easily attached to non-intubated subject) and mainstream capnometers (no time delay, no pump, no sample line plugging). The entire sensor assembly could also be disinfected.

As shown in FIG. 2, the colorimetric indicator 116 can be positioned on a transparent window 118. In some embodiments, the indicator 116 is affixed or adhered to the window 118. The transparent window 118 allows the transmission of light to a surface of the indicator. The transparency also allows reflectance of the light from the indicator to an electro-optical assembly 120 coupled to the colorimetric indicator. In other embodiments, the window 118 may be a plate or substrate that is substantially optically clear such that visible light can transmit (and reflect) therethrough.

In some embodiments, the colorimetric chemistry indicator is contained within a clear sealed plastic gas filled cell while allowing the sensor to record the color. After this "span" calibration to a known gas concentration is recorded in the processor, the operator is then prompted to peel off the plastic gas filled cell exposing the indicator to the environment (e.g. ambient air) and at that time the processor will perform a "zero" calibration point before attaching the indicator/sensor to the subject. Alternate calibration techniques may employ inserting a known color sample unaffected by the presence of $CO_2$ while still reflecting light back to the sensor. As described, in other embodiments, calibration methods may incorporate a ratiometric, dual wavelength electro-optical measurement system which rejects common mode interferences.

The electro-optical assembly 120 may include one or more pulsed light emitters or sources such as an LED. Each light emitter transmits a known wavelength of light to a surface of the indicator 116 through the transparent window. Varying amounts of light will reflect from the indicator 116, which is undergoing color shift from exposure to $CO_2$, back toward the electro-optical assembly 120. A photodetector such as a photodiode detects the amount of reflected light resulting from the color shift and generates a $CO_2$ concentration signal that is transmitted to an electronics module 124. In some cases, a cable 122 couples the electro-optical assembly 118 to the electronics module 124.

The electronics module 124 may include a power supply (e.g. battery) for the system 103. Advantageously, embodiments contemplated will require low power for operation. Many hours of operation are contemplated with the use of hearing aid batteries. In other embodiments rechargeable Lithium ion batteries may be employed as a power source.

In other variations, the electronics module 124 has a microcontroller or processor configured to operate the system. In further variations, the processor/microcontroller receives the signal(s) generated by the electro-optical assembly and computes a $CO_2$ measurement for the gas sample based on the signal. As part of the $CO_2$ computation, the processor/microcontroller may include calibration data and the methods for the system described herein. The processor can calculate additional characteristics of the gas sample, such as the respiration rate of the user or patient. The calibration data may include a calibration curve specific to the particular colorimetric chemical formulation. The calibration data can also include temperature correction data for the particular colorimetric chemical formulation. The calibration data may be stored in flash memory or in the processor.

In further variations, the system 103 may include an indicator housing that holds the protective shield 114, indicator 116, and transparent window 118. The indicator housing may be disposable, replaceable, or otherwise removable from the system 103. The separate sensor housing may also contain the electro-optical assembly and, optionally, the sensor cable. The sensor housing may be releasably coupled to the indicator housing holding the shield, indicator, and transparent window. This allows removal and replacement of the indicator once indicator use has been exhausted. For example, a chemical colorimetric indicator may last 24 hours of use and require replacement for continued operation of the detection system.

In further embodiments, an indicator unit that includes the indicator, a protective shield, and an optically transparent substrate may be integrated with a user interface to detect a breath sample from the nose or mouth. For example, the indicator unit may be formed as a nasal or oral interface that is easily attached near, on, or adjacent to an airway or airflow. The indicator unit may be clipped, for example, to the nose to monitor and measure a patient's $CO_2$ levels. In some embodiments, a disposable indicator unit can be attached and detached from a reusable electro-optical sensor assembly. This could include a tiny magnetic latching mechanism or any other suitable attachment means. Other means of attachment/detachment could employ a plastic molded snap on-off mechanism or a quarter-turn latch mechanism.

FIG. 2 shows a display module 126 may be either hardwired or wirelessly connected to the electronics module 124. The display module may include a computer such as a mobile device or a handheld device that is capable of displaying instructions, $CO_2$ measurements, or a breathing protocol. In further embodiments, the electronics module 124 and display module 126 are a single unit or device. The entire system 103 may be portable and/or handheld.

Figure 3A:
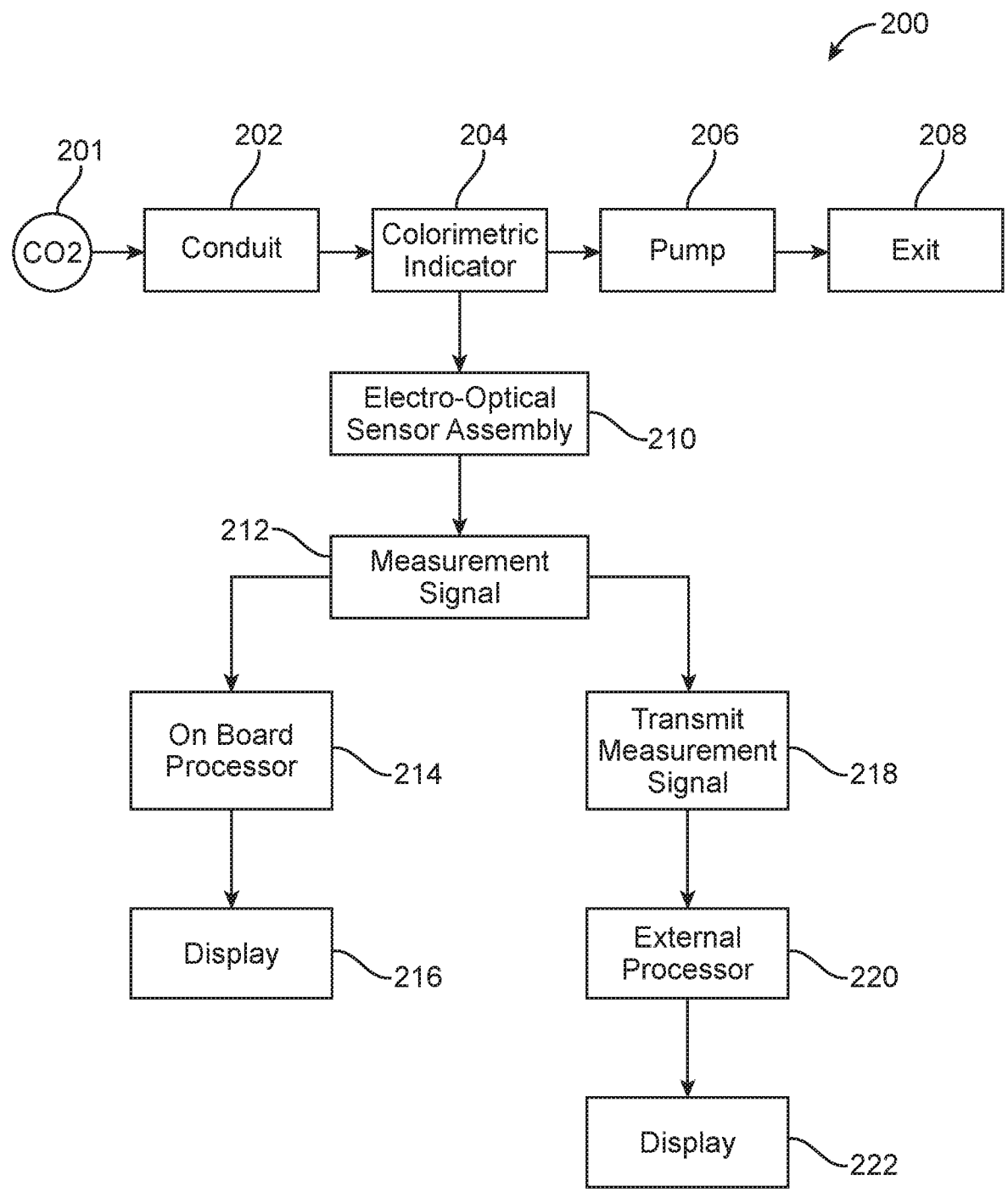
FIGS. 3A-3B illustrate process flow charts in accordance with some embodiments.
Figure 3B:
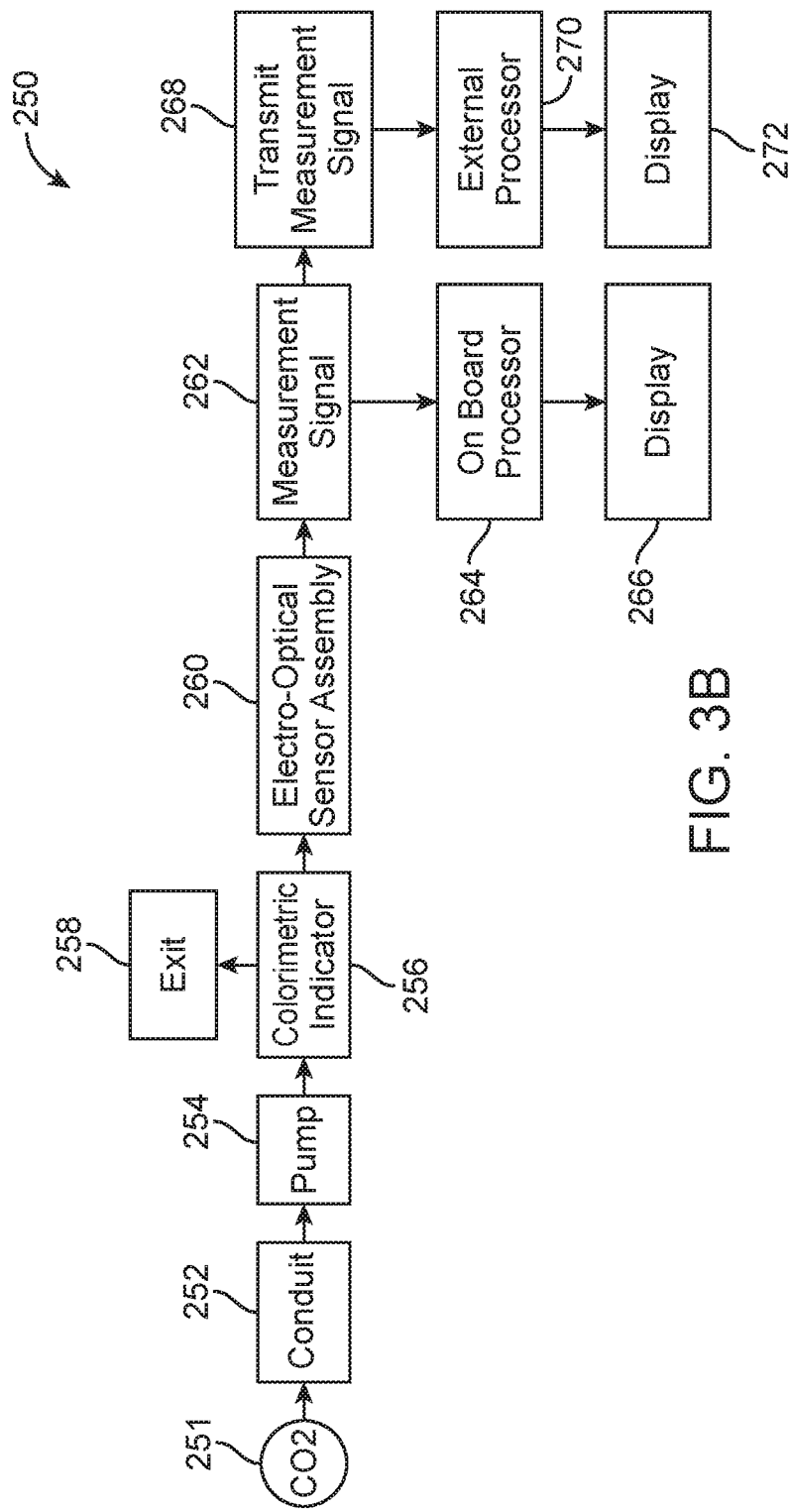

FIGS. 3A and 3B illustrate embodiments of flow charts 200, 250 for process flows. As shown in FIGS. 3A-3B a carbon dioxide sample 201, 251 enters a gas or fluid conduit 202, 252 and contacts the colorimetric indicator 204, 256. A pump 206, 254 can be used to pump the carbon dioxide into contact with the colorimetric indicator. The pump can be downstream of the colorimetric indicator (FIG. 3A) or upstream of the colorimetric indicator (FIG. 3B). The carbon dioxide can exit 208, 258 the system after contacting the colorimetric indicator 204, 256. The electro-optical sensor assembly 210, 260 interrogates the colorimetric indicator 204, 256 when the carbon dioxide stream contracts the colorimetric indicator 204, 256. The electro-optical sensor assembly 210, 260 outputs a measurement signal 212, 262 based on the interrogation of the colorimetric indicator 204, 256. The measurement signal 212, 262 can be sent to an onboard processor 214, 264 that analyzes the measurement signal 212, 262 to determine the amount of carbon dioxide contacting the colorimetric indicator 204, 256. As an alternative option the measurement signal 212, 262 can be transmitted to an external processor 220, 270 with the external processor determining the amount of carbon dioxide that contacts the colorimetric indicator 204, 256. Data associated with the interrogation of the colorimetric indicator can then be displayed 216, 222, 266, 272. The display can be onboard the device (216, 266), external to the device (222, 272), part of a tablet, smartphone, or computer in communication with the device.

Figure 4:
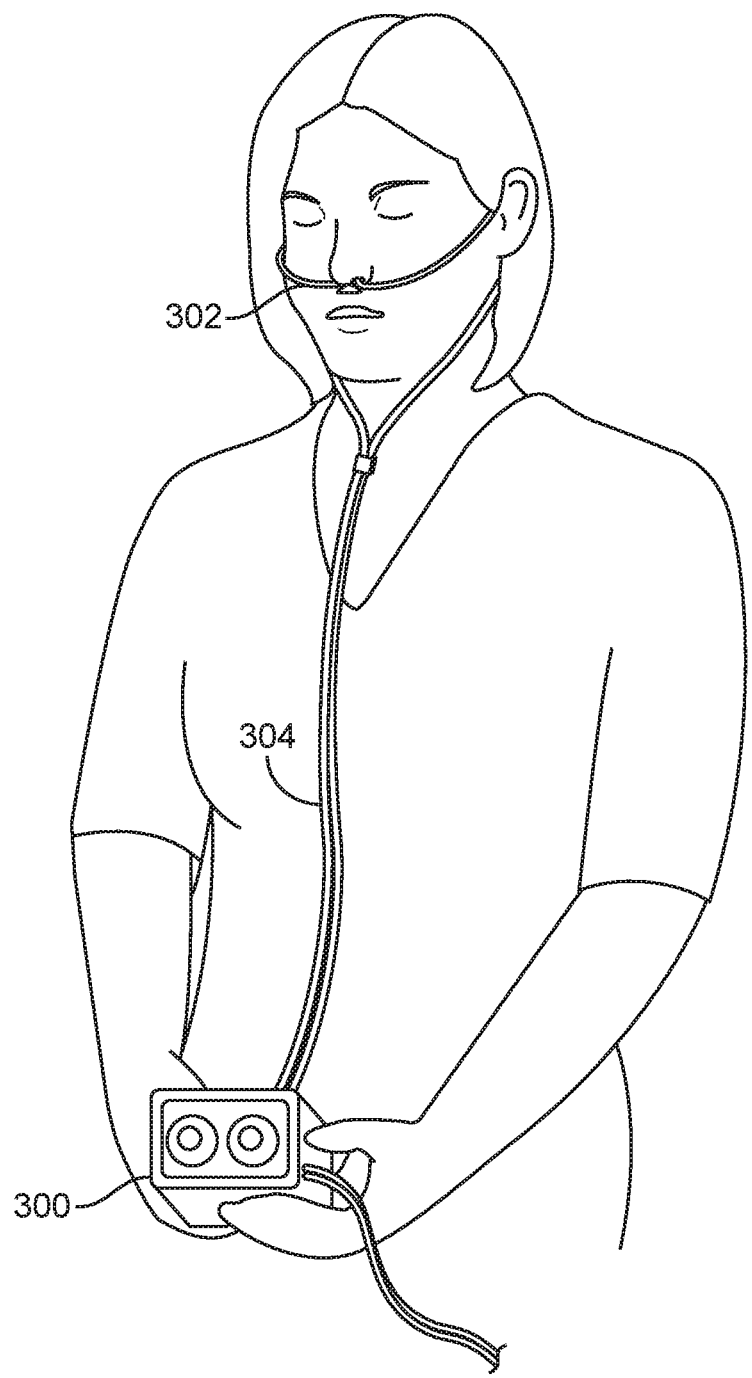
FIG. 4 illustrates a quantitative colorimetric gas detector in accordance with some embodiments.

FIG. 4 illustrates an example of a patient using a quantitative colorimetric carbon dioxide measuring system 300 in some embodiments. Exhaled breath of the patient enters an inlet 302, illustrated as a nasal cannula, and flows through a conduit or cannula 304 and into the quantitative colorimetric carbon dioxide measuring system 300.

Figure 5:
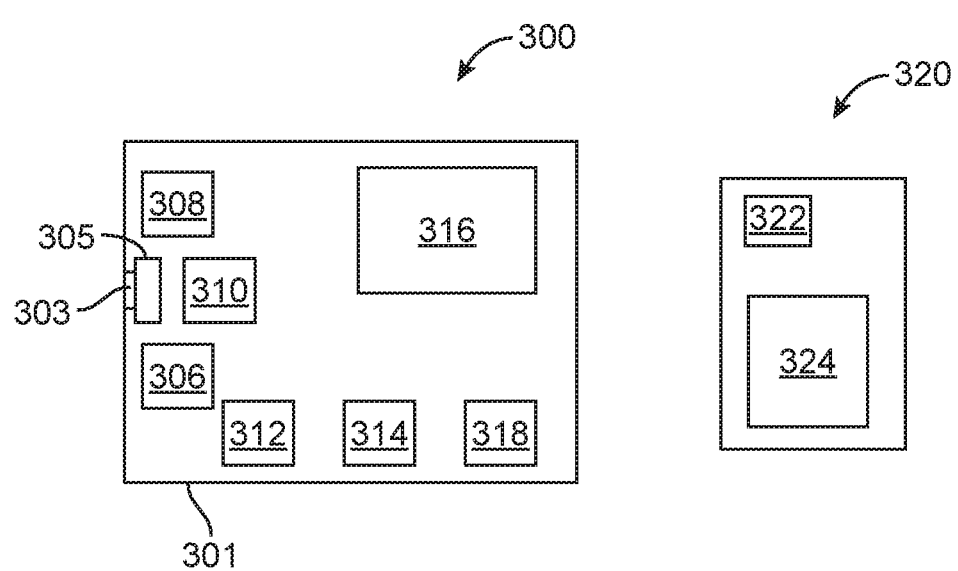
FIG. 5 illustrates a quantitative colorimetric gas detector in accordance with some embodiments.

FIG. 5 illustrates a schematic of a quantitative colorimetric carbon dioxide measuring system 300 in accordance with some embodiments. The system 300 includes a conduit or inlet 303. The conduit or inlet 303 can be configured to receive or engage with a cannula, sample inlet tube, or other conduit such that the cannula, conduit, or inlet is configured to introduce a gas sample to the system 300. FIGS. 6A-6D illustrate various configurations of sample tube assemblies that can be connected to the system 300 via conduit or inlet 303. In some embodiments the gas conduit includes or is configured to removably engage with a separate disposable sample inlet tube. In some embodiments the gas conduit includes or is configured to removably engage with a nasal and/or oral cannula adapted for collecting a sample of a user's exhaled breath for exhaled carbon dioxide measurement with the nasal and/or oral cannula configured to be in fluid communication with the gas conduit.

The system 300 can include a colorimetric indicator 305 within a housing 301 of the system 300. An electro-optical sensor 306 can be included to interrogate the colorimetric indicator 305.

A temperature controller 308 can be provided to control the temperature of the colorimetric indicator and/or the temperature of the incoming gas sample. The temperature controller can control a heater and a cooler to control the temperature of the colorimetric indicator and/or incoming gas sample to a pre-determined temperature. In some embodiments the pre-determined temperature is from about 20° C. to about 50° C. In some embodiments the processor can be configured to control the temperature controller. In some embodiments the temperature controller can also be configured to control a temperature of the electro-optical sensor. In some embodiments a temperature probe can be used to measure the temperature of the colorimetric indicator, incoming gas sample, and/or electro-optical sensor.

A pump 310 can be included within the housing 301 to pump the incoming gas sample. In some embodiments the pump 310 can be located downstream of the colorimetric indicator to effectively pull the incoming gas sample passed the porous colorimetric indicator. In some embodiments the pump can be upstream of the colorimetric indicator to pump the gas sample passed the colorimetric indicator. In embodiments including a heater as part of the temperature controller, the pump can improve heat transfer between the colorimetric indicator and heater by increasing contact between the colorimetric indicator and heater.

The system 300 includes operating electronics 312. The operating electronics can control the system to perform various processing steps as described herein. In some embodiments the operating electronics receive the measurement signal from the electro-optical assembly and calculate properties associated with the measurement signal. In some embodiments the operating electronics receive the measurement signal and send the measurement signal to a processor external to the system 300, with the external processor performing the calculations and analysis of the measurement signal. In some embodiments the system 300 includes a wireless transmitter 314 to transmit data to an external processor, such as a processor on a computer, tablet, or smartphone.

The system 300 can include a power supply 318 to power the components of the system 300.

In some embodiments the system 300 can include a display 316 with the housing 301. In some embodiments the display is external to the system. For example, the display data can be wirelessly transmitted to a device having a display, such as a computer, smartphone, tablet, flat screen monitor, television, etc. In some embodiments a tablet or smartphone 320 can be used with the system 300. The tablet 320 can include a processor 322 and display 324. In some embodiments the processor 322 can receive the measurement signal transmitted by the system 300 and analyze the measurement signal to determine properties associated with the measurement signal. In some embodiments the processor 322 is configured to receive data from the system 300 and display the data on the tablet 320 display 324. Decreasing the processing steps performed by the processor on board the system 300 can reduce the complexity and cost of the system 300.

FIGS. 6A-6D illustrate configurations of sample tube assemblies in accordance with some embodiments. The sample tube assemblies illustrated in FIGS. 6A-6D can be used with the systems 300 illustrated in FIGS. 4 and 5. For example, the sample tube assemblies illustrated in FIGS. 6A-6D can be configured to plug in to or snap into engagement with the system 300. The sample tube assemblies illustrated in FIGS. 6A-6D can be disposable/configured for a single use.

Figure 6A:
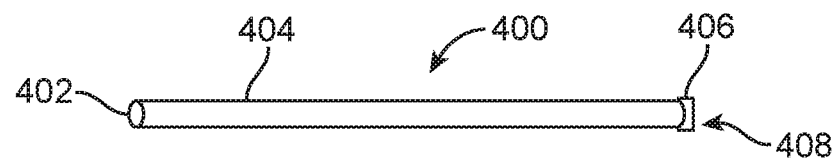
FIGS. 6A-6D illustrate sample tube assemblies in accordance with some embodiments.

FIG. 6A illustrates a sample tube assembly 400 having an inlet 402 and tube, conduit, or cannula 404. The sample tube assembly 400 can be engaged with a replaceable colorimetric material or cartridge 406. The colorimetric material 406 can removably engage with the tube, conduit, or cannula 404. An end 408 of the sample tube assembly can snap into the inlet 303 of the system 300 such that the colorimetric material 406 can be interrogated by the electro-optical sensor 306. In some embodiments the sample tube assembly 400 is designed for a single use. In some embodiments the sample tube assembly 400 can be used multiple times with the colorimetric material 406 periodically replaced. When the sample tube assembly 400 is used with embodiments of the system 300, the colorimetric material would be provided by the sample tube assembly 400 and would not be included within the housing 301 of system 300.

Figure 6B:
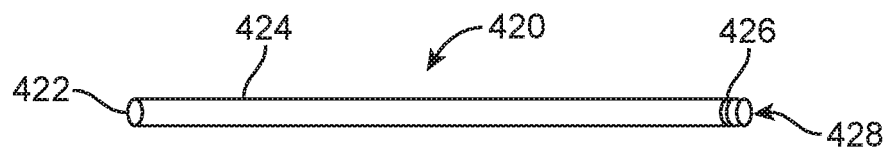

FIG. 6B illustrates a sample tube assembly 420 with an inlet 422, tube/conduit/cannula 424, and a built in colorimetric material 426 at end 428. The sample tube assembly 420 end 428 can engage with the inlet 303 of the system 300 such that the colorimetric material 426 can be interrogated by the electro-optical sensor 306. The sample tube assembly 420 can be designed for single use such that the sample tube assembly 420 can be used until the colorimetric material 426 expires. When the sample tube assembly 420 is used with embodiments of the system 300, the colorimetric material would be provided by the sample tube assembly 400 and would not be included within the housing 301 of system 300.

Figure 6C:
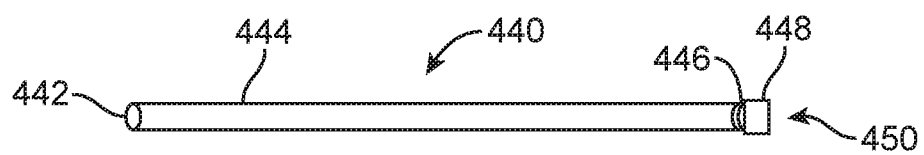

FIG. 6C illustrates a sample tube assembly 440 with an inlet 442, tube/conduit/cannula 444, and built in colorimetric material 446 with gas chamber 448 at end 450. The sample tube assembly 440 can engage with the inlet 303 of the system 300 such that the colorimetric material 446 can be interrogated by the electro-optical sensor 306. The sample tube assembly 440 can be designed for single use such that the sample tube assembly 440 can be used until the colorimetric material 446 expires. When the sample tube assembly 440 is used with embodiments of the system 300, the colorimetric material would be provided by the sample tube assembly 400 and would not be included within the housing 301 of system 300.

Figure 6D:
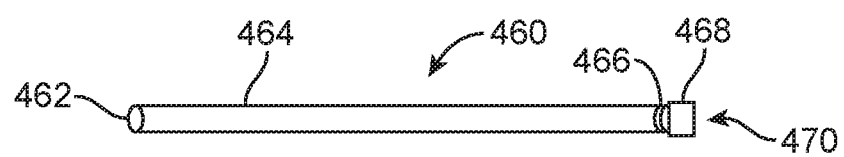

FIG. 6D illustrates a sample tube assembly 460 with an inlet 462, tube/conduit/cannula 464, colorimetric material 466, and electro-optical sensor 468 at end 470. The sample tube assembly 460 can engage with the inlet 303 of the system 300 such that the colorimetric material 466 and electro-optical sensor 468 can communicate with the system 300. The sample tube assembly 460 can be designed for single use such that the sample tube assembly 460 can be used until the colorimetric material 466 expires. When the sample tube assembly 460 is used with embodiments of the system 300, the colorimetric material and electro-optical sensor would be provided by the sample tube assembly 400 and would not be included within the housing 301 of system 300.

The inlets 402, 422, 442, and 462 of sample tube assemblies 400, 420, 440, and 460 can be connected to the user or patient by any of the structures illustrated herein or by conventional techniques. The inlets 402, 422, 442, and 462 can also be coupled to accessories configured to attach to the user's nose or mouth. For example, the inlets 402, 422, 442, and 462 can be configured to removably engage with and couple to a nasal and/or oral cannula adapted for collecting a sample of a user's exhaled breath for exhaled carbon dioxide measurement. In some embodiments the inlets 402, 422, 442, and 462 can be configured for use with intubated patients.

The quantitative colorimetric carbon dioxide measuring system may include computer software instructions or groups of instructions that cause a computer or processor to perform an action(s) and/or to make decisions. In some variations, the system may perform functions or actions such as by functionally equivalent circuits including an analog circuit, a digital signal processor circuit, an application specific integrated circuit (ASIC), or other logic device. In some embodiments, the image recording system includes a processor or controller that performs the functions or actions as described. The processor, controller, or computer may execute software or instructions for this purpose.

"Software", as used herein, also known as firmware includes but is not limited to one or more computer readable and/or executable instructions that cause a computer or other electronic device to perform functions, actions, and/or behave in a desired manner. The instructions may be embodied in various forms such as objects, routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software may be dependent on, for example, requirements of a desired application, the environment it runs on, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

Patient Interface

There are many different methods of attaching the colorimetric $CO_2$ sensor to the patient or otherwise interfacing with the patient. Those methods may be different for different applications in the home, pre-hospital or clinical. Some of these methods are, but not limited to: over the ears similar to a nasal sampling cannula, a boom-like structure similar to a wireless headset with sensor placement near the nares; a nasal alar clip; elastic band with cup collection chamber for sensing oral/nasal exhaled air; an inline airway adapter for use with intubated patients; a non-toxic (peel and stick) adhesive sensor assembly attachment to the nares or upper lip with an ear clip cable strain relief; incorporate sensor and electronics into a pair of eyeglasses with an optional heads up display of $CO_2$ concentration and respiration rate; a headband containing the sensor/cable, electronics and power supply wirelessly connected to the remote display. Any of these attachment structures can be used with the devices disclosed herein. In some embodiments the devices described herein can be designed for use with intubated patients.

FIG. 4 illustrates an example of a patient using a sidestream embodiment of a quantitative colorimetric carbon dioxide measuring system 300 with a sample tube that is in an over-the-ear attachment mechanism. Exhaled breath of the patient enters an inlet 302, illustrated as a nasal cannula, and flows through a conduit or cannula 304 and into the quantitative colorimetric carbon dioxide measuring system 300. The inlet 302 can be clipped to the nose, e.g. the nasal alar cartilage.

Figure 7:
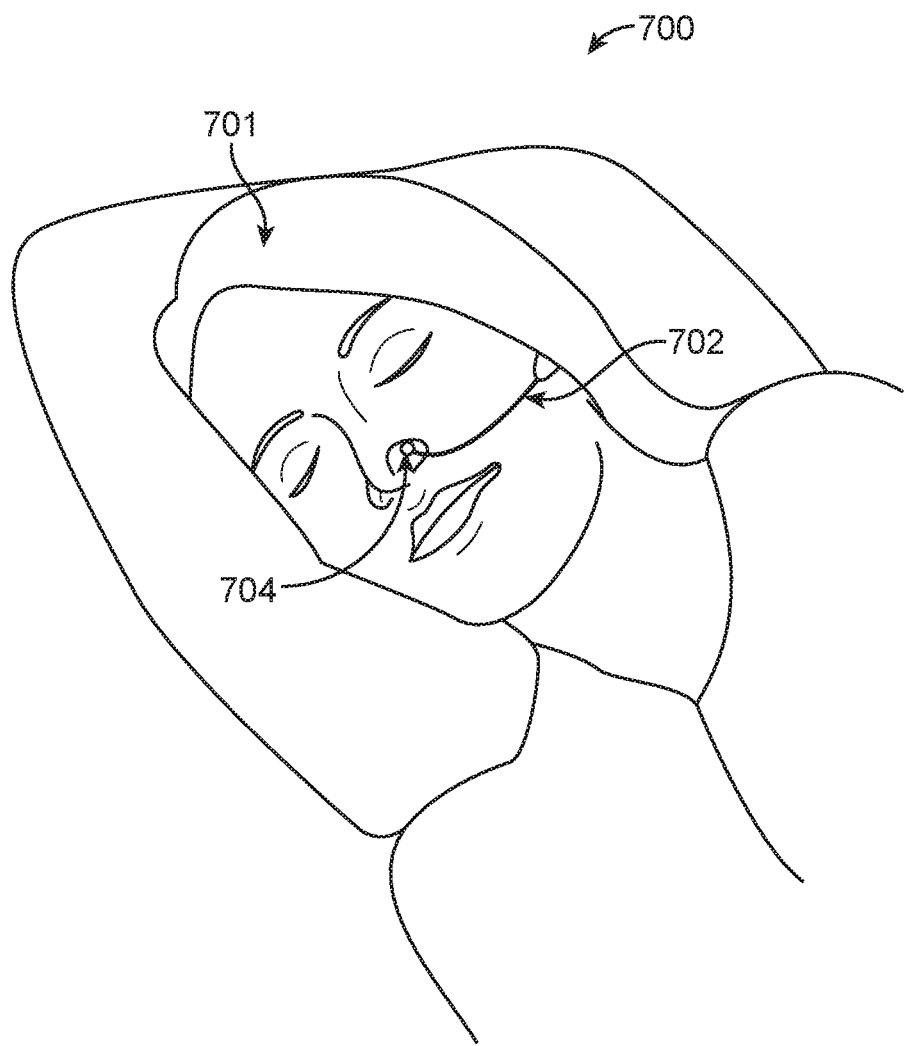
FIG. 7 shows an exemplary patient attachment mechanism with integrated gas sensors in accordance with some embodiments.

FIG. 7 shows an exemplary embodiment of a quantitative colorimetric $CO_2$ detection system with a patient attachment mechanism. In some embodiments, the sensing unit 704 contains the colorimetric indicator and the electro-optical sensor assembly. In further variations, the sensing unit 704 may include a protective shield and optically clear indicator substrate as described above. The sensing unit 704 may be attachable to the patient by way of clips that attach to the nose, e.g. nasal alar cartilage.

In further embodiments, a small flexible insulated wire cable 702 leads from the sensing unit 704 back to an electronic module, which is located on a headband or a headphone embodiment. The colorimetric $CO_2$ sensor could be combined with a pulse oximeter sensor on the same nasal alar site, expanding use to other monitoring applications.

In further variations, an adjustable (malleable) rod or boom-like structure may be used to adjustably position the sensing unit 704 in the patient's nasal airflow. In some cases, a connecting cable may run through the malleable rod to connect the sensing unit to an electronic module.

As shown in FIG. 7, in some cases, the patient relaxes and breathes through her/his nose to provide a breath sample for $CO_2$ measurement.

Figure 8:
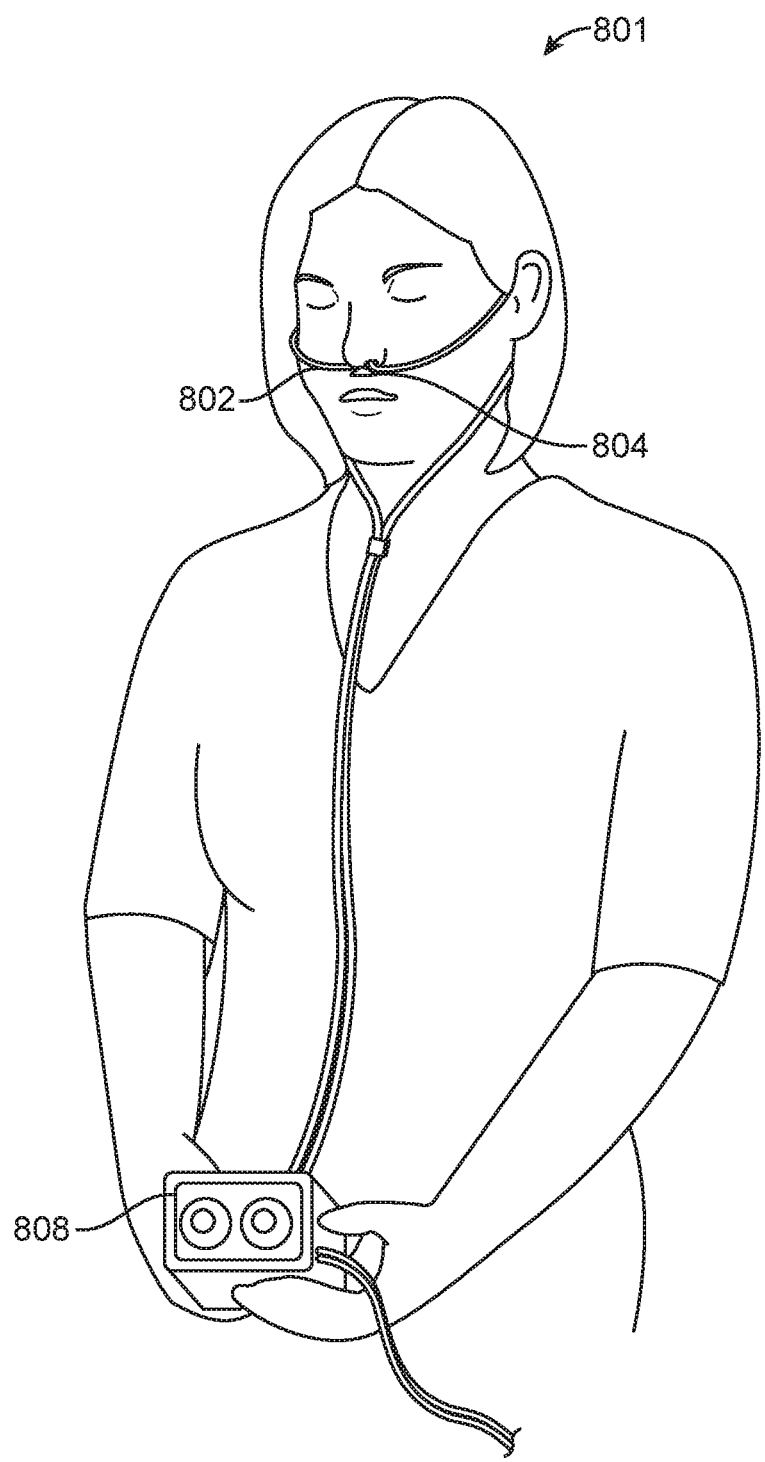
FIG. 8 shows a quantitative colorimetric gas component detector with a nasal airflow sensing unit in accordance with some embodiments.

FIG. 8 shows another example of a patient attachment mechanism where the sensing unit 804 is attached to straps or cables 802 that connect to a handheld electronics module 808 that can optionally include a display.

Figure 9:
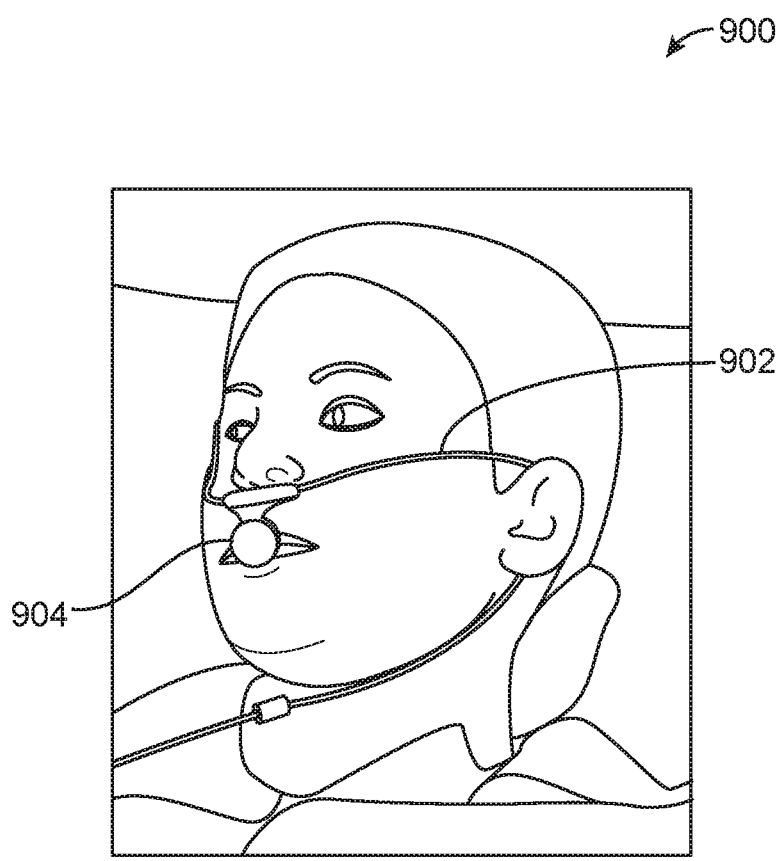
FIG. 9 shows a quantitative colorimetric gas component detector with a nasal and oral airflow sensing unit in accordance with some embodiments.

Referring to FIG. 9, a wearable quantitative colorimetric $CO_2$ detector system having a patient attachment mechanism is shown. The system 900 shown is capable of sampling both nasal and oral breathing patterns. The system 900 may be configured to alternate between sampling nasal or oral breath. Alternatively, the system may also sample only nasal or oral breath per measurement. As shown, the $CO_2$ colorimetric sensing unit 904 may include one or more inlets to both the nasal and oral airways. The sensing unit 904 may optionally operate a single inlet to allow either nasal or oral air to enter the sensing unit. In other variations, the sensing unit may include more than one inlet for capturing an air sample from either the nasal or oral airflow. In some variations, two or more separate indicator/sensor assemblies may be used to test air from each or either nasal and/or oral source. Cable 902 is coupled to the sensing unit 904 and is in electrical communication with an electronics module. In some cases, the electronics module is located remote from the patient. In other variations, the electronics module is integrated into a wearable article such as a headband.

In a further embodiment, the sensing unit 904 may include the indicator and the electro-optical sensor assembly. Alternatively, the sensing unit 904 may include the indicator and a light guide such as an optical fiber may optically couple the indicator to a remotely located electro-optical sensor assembly. For example, the colorimetric indicator chemistry may be affixed at the end of a plastic optical fiber with the electro-optics components at the other end. This could be useful in MRI imaging applications.

Various embodiments of wearable electronics modules would permit private, unrestricted, unobtrusive mobility and portability. More importantly, a wearable device would also allow the subject's hands to be unencumbered allowing other functions (eating, washing hands, holding reading material, writing, phone calling, etc.) The battery operated system could be used while the subject is ambulatory, sleeping and/or doing daily activities without being tethered to a restrictive sampling line, a bulky electronics/display module or power cord. These various embodiments would include but not limited to the electronics module: affixed or integrated into a headband, placed on back side of ear (like a hearing aid), contained within an audio headset or enclosed with lanyard worn around the neck. In all these wearable embodiments, the electronic module may employ Bluetooth wireless connectivity to remote display/storage devices (custom unit, smartphone, tablet, laptop, etc.)

Figure 10:
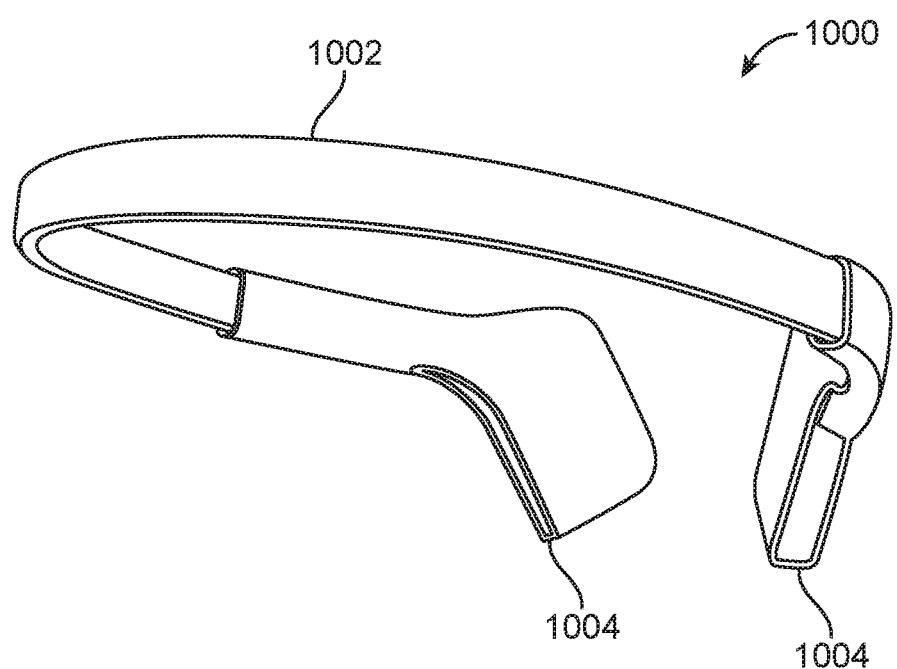
FIG. 10 shows a headband for a quantitative colorimetric gas component detector system in accordance with some embodiments.

FIG. 10 shows a headband 1000 with a headband portion 1002 and ends 1004. The headband depicted incorporates the electronics module within the headband portion and/or ends 1004. The headband 1000 includes a connection port for coupling to a sensing unit as described above. A flexible sensor cable (not shown) may be used to couple the sensing unit to the headband electronics module. The sensing unit may be attachable to an airflow airway structure such as the nasal alar as suggested above.

Figure 11:
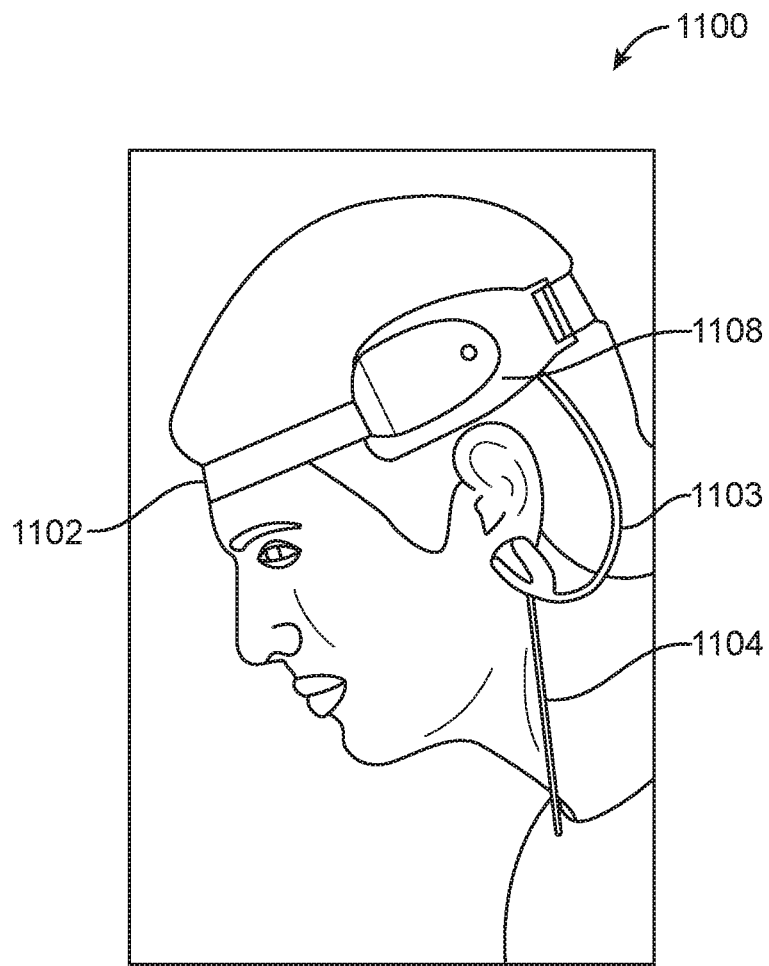
FIG. 11 shows a headband for a quantitative colorimetric gas component detector system with an attached sensing unit at the distal end of a flexible cable in accordance with some embodiments.

FIG. 11 shows an alternate headband 1100 configuration depicting a similar cable attachment 1103 and a sensing unit 1104. The electronics module may be contained in the headband such as at the lateral caps 1108. In some embodiments, the wearable units described can connect through wired or wireless means to a processor or a display (e.g. smart phone) for operation of the detection systems. Instead of an ear attachment, the sensor could be clipped to the nasal alar.

Figure 12:
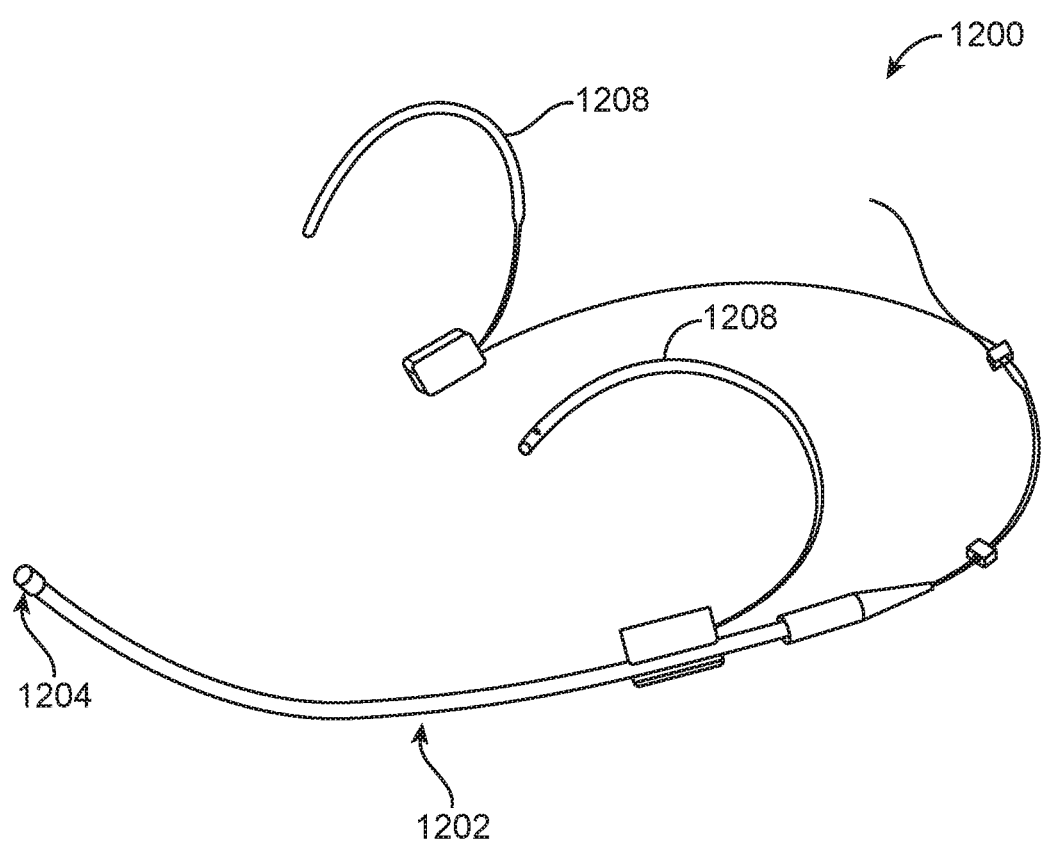
FIG. 12 shows a wearable quantitative colorimetric gas component detector system in accordance with some embodiments.

FIG. 12 shows another wearable colorimetric carbon dioxide detection device 1200. The device 1200 includes two ear pieces 1208 and a malleable rod or boom-like structure 1202 with a sensing unit 1204 at the distal end. The addition of a microphone may be employed to allow the user to record audible messages. The device 1200 may include a cable leading from the head worn attachment to a belt-worn remote electronics module.

Figure 13A:
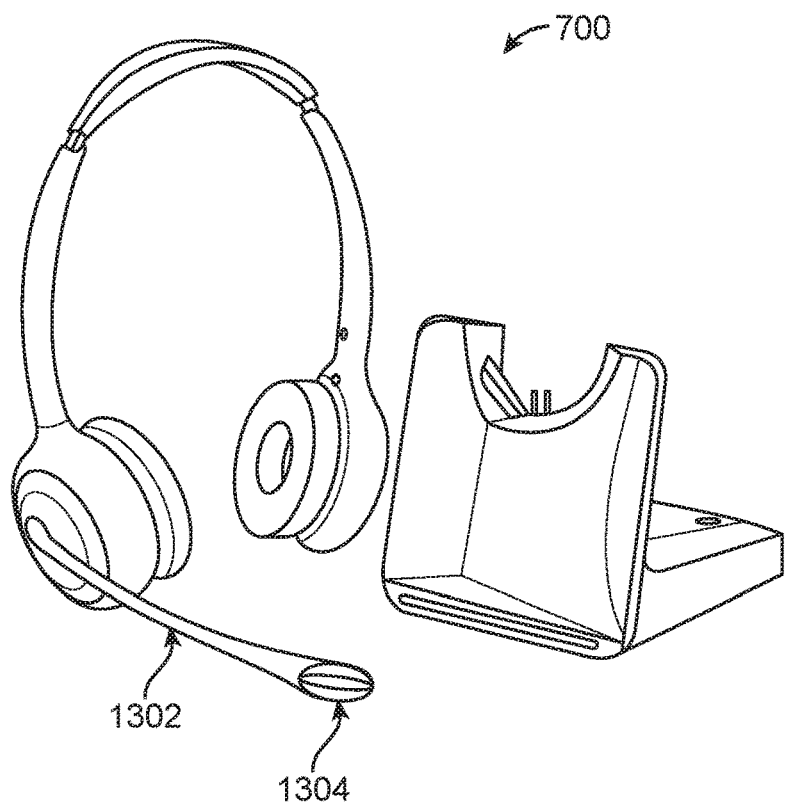
FIGS. 13A-13B shows a wearable a quantitative colorimetric gas component detector system according to some embodiments in accordance with some embodiments.
Figure 13B:
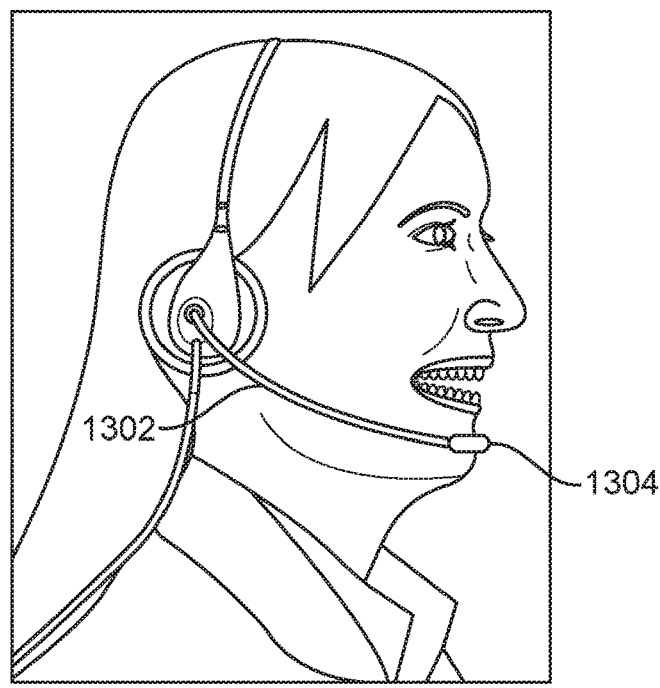

FIGS. 13A-13B depicts a headphone embodiment. As shown, the electronics module and battery would be incorporated into the headphones. The headphones 1300 would enable private audible commands, alerts, breathing instructions, (calming music), etc. thus eliminating the need for the subject to visually watch a remote digital display module. In certain applications and clinical situations, this embodiment may even eliminate the requirement for the separate remote visual display module. With the headphones securely in place, an adjustable (malleable) connecting rod 1302, incorporating the sensor wiring, the colorimetric sensor 1304 and an optional microphone is positioned near the subject's nose and mouth.

In some embodiments the colorimetric film can be part of a disposable portion of the device. For example, the colorimetric indicator film can be included with or integral with a disposable inlet or sample tube assembly. FIGS. 6A-6D illustrate embodiments of disposable sample tube assemblies. The colorimetric indicator film can be provided as a removable and disposable module that engages with the inlet tube assembly. The colorimetric indicator film can be provided with the electro-optical module. The colorimetric indicator film can be removable relative to the electro-optical module. The colorimetric indicator film can be provided with or as part of an assembly including a protective shield designed to reduce ambient light.

For intubated spontaneous breathing patients the device can be similar to the sidestream embodiments disclosed herein. For example, the inlet could include a disposable assembly containing the colorimetric indicator film as illustrated in FIGS. 6A-6D. The disposable assembly can allow the operator or patient to easily and conveniently attach and remove the assembly from an electro-optical sensor assembly at some predetermined cycle to ensure system performance. The disposable assembly containing the colorimetric film can be replaced when needed.

Locating the electro-optical assembly further away from the patient's mouth can have a number of design advantages. Locating the electro-optical assembly further away from the patient's mouth/nose can make it easier to isolate the sensor from environmental effects like temperature variation and ambient light. A larger and cheaper electro-optical assembly can also be used when it is not located in close proximity to the user's mouth. In addition, locating the sensor assembly further away from the patient's mouth reduces damage and wear and tear on the electro-optical assembly. Locating the electro-optical assembly away from the patient's nose and mouth also allows for a less bulky and intrusive sample collection adjacent to the patient's nose and mouth.

A sample tube can be used to receive a portion of the gas stream sample from the subject's breath and conducting it via a small, disposable, inexpensive cannula to the electro-optical sensor. The sample tube can be connected to a remote enclosure containing the gas sensor and processing electronics. The sample tube can be connected to any of the embodiments of sample tube assemblies illustrated in FIGS. 6A-6D. In most cases the sampling line is a small diameter plastic assembly. The sampling line can be affixed to the patient in an "over-the-ears" fashion depicted in FIGS. 7-9, 12, and 13A-13B. Over-the-ears subject attachment can be used for clinical monitoring of both sedated and conscious subjects. For those few subjects who dislike or object to wearing the over-the-ears cannula, alternate patient attachments can also be used. Additionally, an exhaled gas collection cup could be employed near the end of the sample line to enhance sampling of exhaled gas simultaneously from both the subject's nose and mouth.

In another example, the colorimetric sensor can be located in close proximity to the patient's nose or mouth to receive the exhaled gas with a fiber optic cable connecting the colorimetric sensor color to the remote electro-optical assembly.

The advantages of enclosing the colorimetric indicator sensor and associated electronics inside a remote enclosure are multifold with the sampling tube embodiments. First and foremost, a "light tight" remote enclosure can prevent ambient light from interfering with the sensor. The remote enclosure can facilitate isolating the colorimetric indicator from reflected visible light interference. In addition, the somewhat fragile electro-optical components and colorimetric film can be located further away from the user's mouth, making the electro-optical sensor less likely to be subject to spills, loss, or other forms of damage or user abuse.

The sidestream configurations the colorimetric indicator can also be less susceptible to temperature variations in the ambient environment and the patient's expired air. The exhaled breath sample is aspirated through the sampling cannula, such as the sample tube assemblies illustrated in FIGS. 6A-6D, such that the temperature of the exhaled breath sample equilibrates to the ambient air temperature before contacting the colorimetric sensor indicator thereby reducing temperature variation effects. In some embodiments a thermal sensor or probe can be placed inside the sensor chamber to provide further temperature compensation. In another alternative a temperature controller, such as a micropower temperature controller, can be used to hold the colorimetric indicator at a constant temperature to improve system accuracy and precision as well as prevent moisture from collecting on the indicator surface. For the sidestream embodiments a pump can be used to pump the breath sample. The pump can be downstream of the colorimetric indicator or upstream of the colorimetric indicator and can improve contact between the colorimetric indicator and the temperature controller.

Additional advantages of embodiments contemplated and described herein include: (a) very low cost-complexity similar to typical portable pulse oximeter sensors and electronic readout; (b) very low power consumption-extremely portable with hearing aid style battery power; (c) simple to self-attach, unobtrusive and comfortable to wear; (d) easy user calibration (simple mechanical action while connecting disposable indicator to sensor); (e) indicator/sensor combo is non-toxic, humidity insensitive, very small, lightweight, waterproof and potentially sterilizable; (f) no sensitivity to anesthetic agents, nebulized medications, visible light, magnetic fields, RF, air particulates, acoustic noise, shock and vibration; (g) no instrument warm up time is required-simple push on button, auto power off, power on/breath detect indicator LED, error messages; (h) no aspirating pump required thus no transit time readout delay and no "sampling line" plugging; (i) home-based biofeedback $CO_2$ concentration monitoring applications—including Panic Disorder, PTSD and Asthma; (j) monitoring capability in pre-hospital emergency medical services, conscious sedation, sleep monitoring, dentistry, veterinary, supplemental $O_2$ therapy, etc.; (k) unique calibration methodology; (l) quantifiable colorimetric $CO_2$ concentration monitoring at respiratory rates up to at least 40 BPM; (m) various patient attachment configurations and embodiments; (n) custom data display presentation; (o) wireless (Bluetooth) data connectivity to tablet computer or smart phone; (p) no routine maintenance of electronic module-indicator has 3 year shelf life; and (r) potential for revenue from disposable indicator that is replaced daily.

Methods of Quantitative Colorimetric $CO_2$ Measurement

Additional embodiments are directed to methods for measuring a component of a patient's breath (e.g. carbon dioxide) using a quantitative colorimetric device or system such as those described herein. For example, referring generally to FIGS. 1-2, a patient may exhale into an inlet 102 of a quantitative colorimetric device. The inlet 102 may direct the entire breath sample or a portion of the exhaled air into an indicator compartment, unit, or testing chamber 115. The indicator unit 115 can include a colorimetric indicator 116 positioned for exposure to the breath sample. Once exposed to the breath sample, the indicator changes colors from a baseline color. The color change is based on the concentration of a component (e.g. carbon dioxide) in the breath sample.

Once the breath sample has been introduced into the measurement device, an electro-optical assembly transmits a reference light to a surface of the indicator. Light reflected back from the surface of the indicator is detected by a photodetector in the electro-optical assembly. The photodetector generates an electrical signal based on the reflected light. The electrical signal is then transmitted to a processor or computer for analysis, such as signal processing, to determine if a color change has occurred and the concentration of the gas component in the breath sample based on any color change. Additionally, the processor may refer to calibration data or a calibration curve for the system in computing the concentration of the gas component in the breath sample. The calibration data may be stored in the processor or elsewhere on the system. For example, each indicator unit may have its own particular calibration data. As such, each indicator unit may include stored calibration data that can be accessed by the processor for quantitative gas concentration calculations. The calibration data may be stored in a flash memory device on the indicator unit.

Once the gas component concentration is determined, the concentration may be displayed on a monitor. The quantitative colorimetric system may include a display monitor or, alternatively, the system may communicate the information to a remote monitor through a wired or wireless connection. The display can be a mobile display device, such as a smartphone or tablet, or a non-mobile display device, such as a television.

Any measurements for a patient may be stored locally on the device or remotely for later retrieval. This allows the patient as well as medical professionals to monitor the tested component's levels in the patient's breath.

In some embodiments, a measuring session includes one or more of the following steps:

(a) Attaching a fresh indicator assembly or unit to the sensor assembly (b) Turning on the electronics module power button (or otherwise activating the electronics module)

(c) Calibrating the measurement system such as by automatically conducting a span calibration by having the sensor "read" the signal from the color associated with a known $CO_2$ concentration. (e.g. electronics module performs calibration)

(d) Removing a calibration ampoule from the indicator assembly or unit (e) Performing a zero calibration (e.g. the electronic module may automatically performs a zero calibration in room air, assumed to be zero CO2)

(f) Attaching an indicator/sensor assembly and/or a sample tube to the patient (such as attaching to the nose alar)

(g) Instructing the user to begin breathing (h) Recording the testing session (e.g. the electronics module may automatically record the test session)

(i) Measuring real-time breath-by-breath gas component concentrations (e.g. partial pressure and/or volume percent)

(j) Computing real time, time varying gas component (e.g. $CO_2$) waveforms.

(k) Computing respiratory rate (l) Monitoring patient parameters (m) Computing end tidal $CO_2$ concentrations if applicable (n) Alerting the user if it detects any measurement errors or artifacts in the measurement process (e.g. electronics module alerts user).

(o) Electronically transmitting data to a remote smartphone, tablet or other internet connected device for subsequent storage, retrieval, sharing and healthcare provider analysis (e.g. wireless or wired transmission).

(p) Prompting the user for certain breathing rate and breathing depth patterns, alerts, instructions, session time and error messages such as "replace indicator", "wireless disconnect" or other malfunctions (e.g. mobile device may perform prompting)

Methods for Breathing Therapy

In addition to the above, various aspects of the inventions are directed to a breathing therapy system for non-invasively and non-pharmaceutically treating various conditions include panic disorder, anxiety, general anxiety disorder, obsessive-compulsive disorder, social phobia, depression, apnea, migraines, epilepsy, asthma, post-traumatic stress disorder, and hypertension. Some embodiments described herein are directed toward breathing therapy to treat a disorder or disease. For example, quantitative colorimetric carbon dioxide detection system described can be used to measure and modify a user's $CO_2$ levels to provide treatment for any number of disorders or illnesses.

Figure 14:
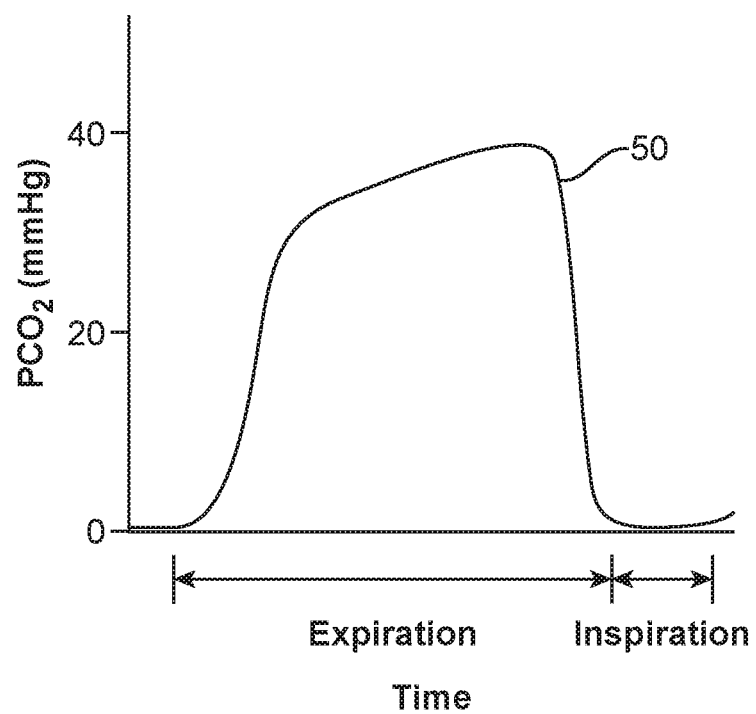
FIG. 14 illustrates an inspiration and expiration graph.

In some cases, a patient's end-tidal $CO_2$ levels are monitored and/or modified. Generally, end-tidal $CO_2$ refers to the carbon dioxide levels measured in a user's exhaled airflow. FIG. 14 provides a general representation of the expiration and inspiration pattern for respiration where end-tidal $CO_2$ is measured at the peak 50 of expiration. End-tidal $CO_2$ levels can be measured in partial pressure units such as mmHg. Additionally, $CO_2$ levels in general, including end-tidal $CO_2$, can be quantitatively measured in terms of concentration. Concentration may be measured in volume percent or pressure. In some embodiments, the carbon dioxide values may be measured in one unit and converted to another. For example, partial pressure values may be derived from measured concentration percentages. In further variations, the carbon dioxide values may be measured in pressure values directly.

As can be appreciated, measuring and modifying end-tidal $CO_2$ levels may be described as a non-limiting example of one treatment application for the quantitative colorimetric gas component detection systems described. $CO_2$ levels measured may include (but is not limited to) end-tidal $CO_2$. Similarly, $CO_2$ may be quantified in terms of partial pressure units (e.g. mmHg) as illustrated in examples described. However, it is to be understood that any units may be used to quantify the amount of $CO_2$ measured from a gas sample (including volume percentage) for the purposes of this disclosure.

As described, some embodiments contemplated provide for a breathing therapy system having a device for measuring the concentration of components in a user's exhaled air. The device may display the measured components in any suitable units including pressure units. The device may include sensors for measuring $CO_2$ levels in the expired air as well as sensors for measuring other parameters of the user such as breathing rate, pulse rate, blood oxygen saturation level, etc.

Figure 15:
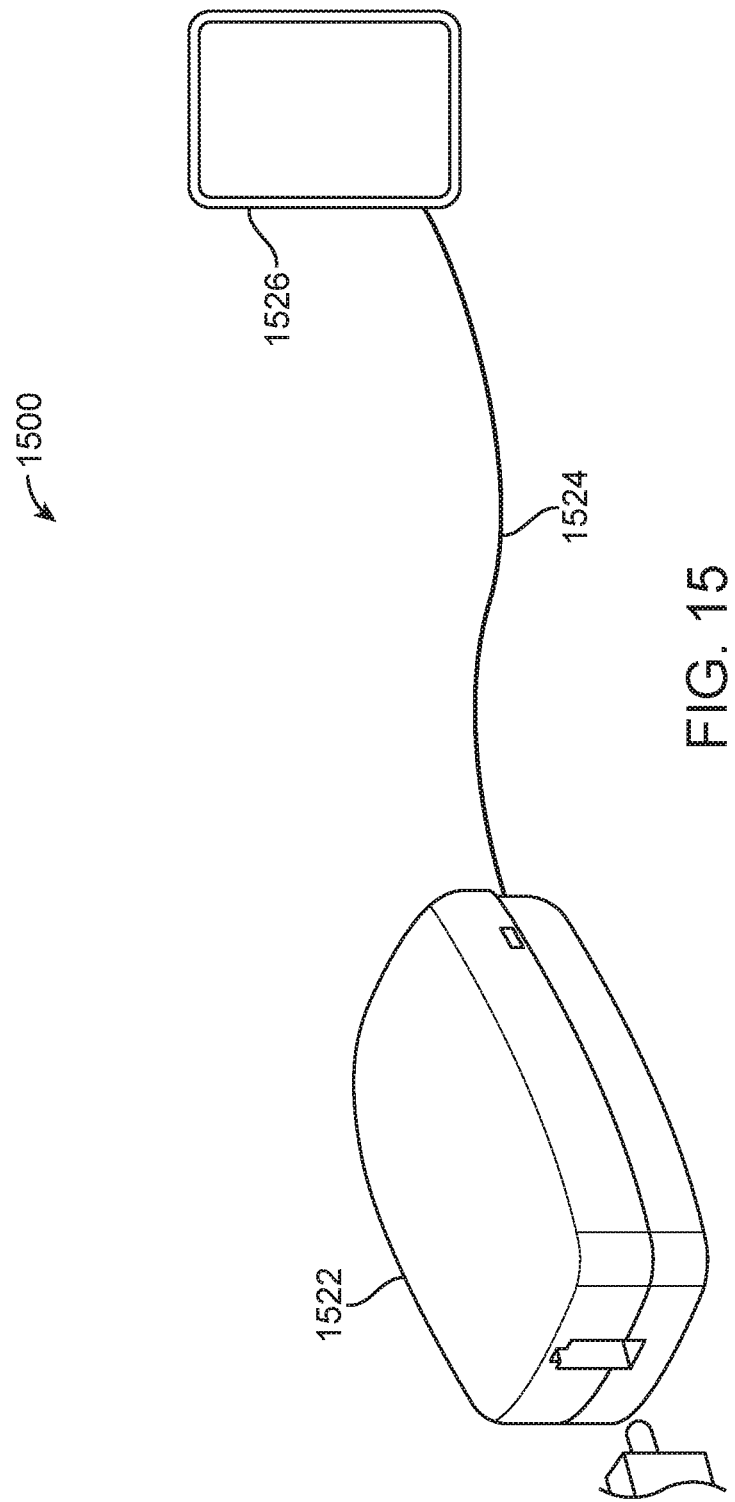
FIG. 15 illustrates a breathing therapy system according to embodiments described.

For illustration purposes, FIG. 15 shows a general quantitative colorimetric capnometer having a main sensing unit 1522 and a connector 1524. The main sensing unit 1522 may include any of the components described such as a colorimetric indicator and an electro-optical sensing assembly. In some embodiments, the breathing system 1520 may further include a display component 1526 for providing measured end-tidal $CO_2$ levels, breathing rate, or any other measured/sensed user information. The display component 1526 may provide numerical values for the measured/sensed information and/or provide a graph showing the user's respiration patterns.

Referring again to FIG. 15, some embodiments provide for $CO_2$ measuring devices that record measured parameters during use. The device, such as a quantitative colorimetric capnometer or an IR absorption spectroscopy sidestream capnometer, may record the information locally within the device for later retrieval by the user or a medical professional. In other embodiments, the capnometer may communicate the user's information through a wired or wireless connection to a centralized database. The capnometer may electronically communicate the user's information to a mobile device such as a smart phone, tablet, laptop, etc. In such cases, the mobile device 1526 may electronically receive the user's information, process the information, and provide the user and clinician/caregiver with a summary or assessment of the user's progress.

Figure 16:
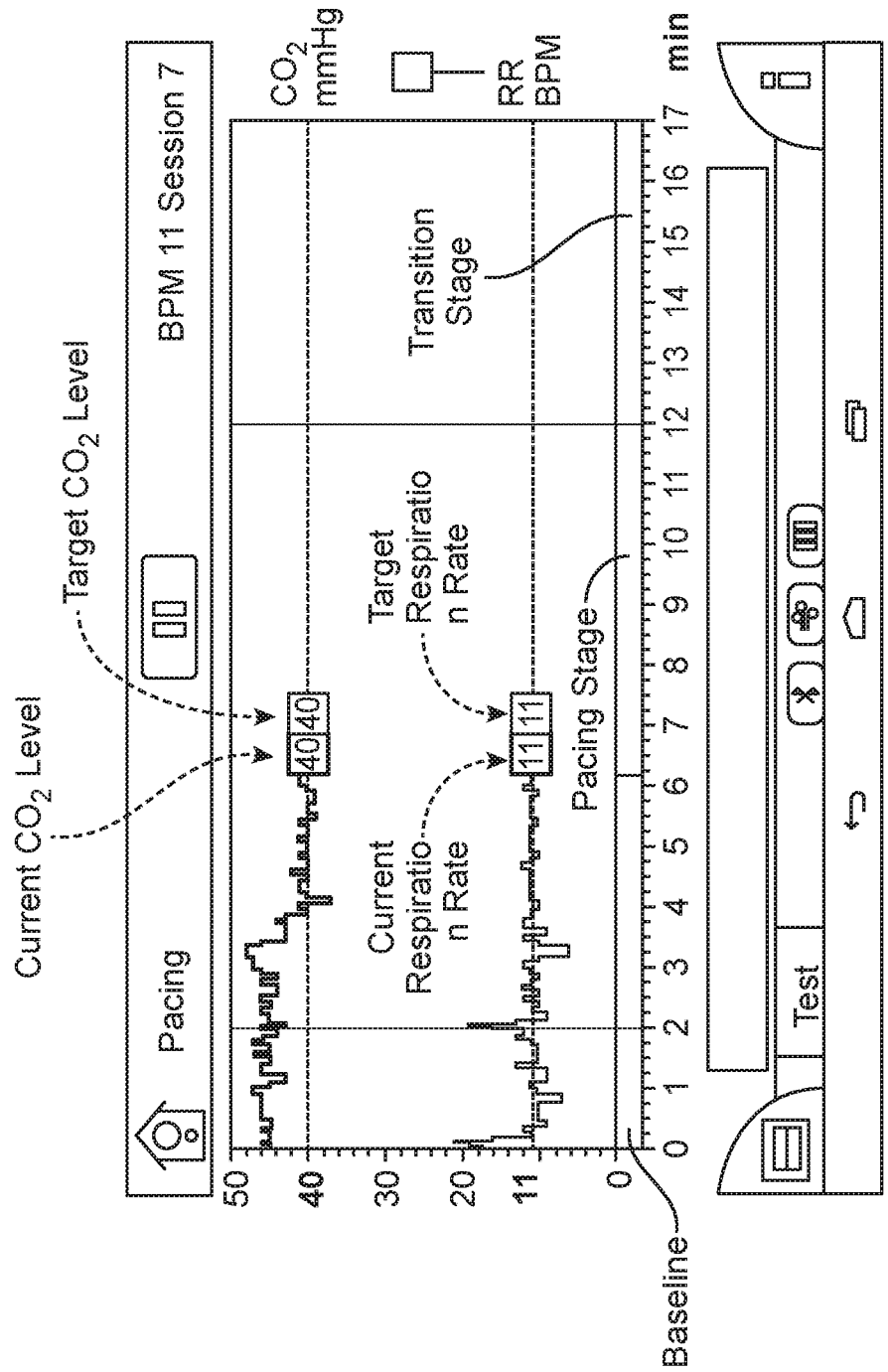
FIG. 16 illustrates a graphical representation of end-tidal $CO_2$ and breathing rate in accordance with some embodiments.

In further embodiments, the capnometer may communicate the user's information to the mobile device 1526 during a patient's use. The mobile device 1526 processes the information in real-time or dynamically to provide the user with a graphical representation of respiratory gas exchange parameters. FIG. 16 shows graphical representation of a user's end-tidal carbon dioxide levels and breathing rate per minute during capnometer use. The mobile device 1526 can receive user information from the capnometer and display such information during use (and/or after use). Alternatively, in some embodiments, the patient's respiration information is measured but not displayed.

To provide breathing therapy, the quantitative colorimetric devices described may include a stored breathing therapy protocol or treatment program that is executed while the patient provides breath samples. For example, the system or device may include a processor with a stored breathing protocol that activates based on the concentration or pressure of end-tidal $CO_2$ measured in the patient's breath sample. The program may use visual or audio cues to guide the patient to a target breathing rate and/or $CO_2$ concentration/pressure. The visual or audio information or cues may be presented to the user through a display screen and/or audio device such as headphones. In some cases, the patient attachment would include a microphone allowing the user to record audible comments (time stamped) during the therapy session thus eliminating the need for manual note taking. As described above, the display screen or audio device may be integrated with the measuring components. (See FIGS. 10-13B).

As an example, some embodiments described provide for breathing therapies, methods, systems and devices that treat a disorder or illness by helping a user modify end-tidal $CO_2$ levels in exhaled air. For example, a user may be guided either visually or audibly to attain or maintain target end-tidal $CO_2$ levels in exhaled breath. In some cases, the desired target end-tidal $CO_2$ level is between about 37 mmHg and about 43 mmHg.

Figure 17:
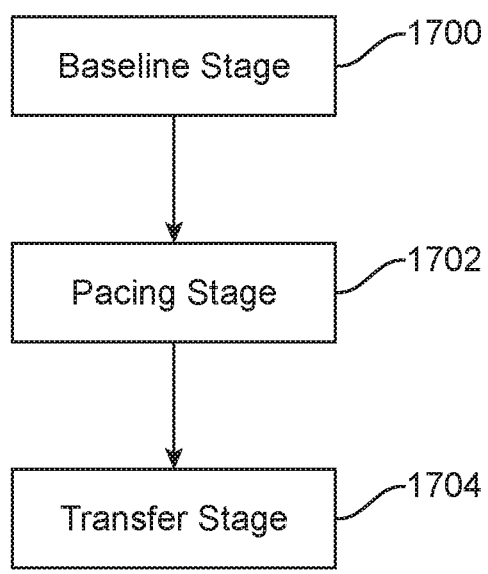
FIG. 17 is a flowchart showing a three-stage treatment protocol according to embodiments described.

End-tidal $CO_2$ modification can be accomplished in several ways according to the described embodiments. For example, as shown in FIG. 17, some embodiments provide for a three-stage therapy for modifying end-tidal $CO_2$. In such embodiments, the first stage can be a baseline stage 1700 where the patient's baseline data is collected. In some cases, the first stage lasts about two minutes. A second stage may be a pacing stage 1702 during which the patient is instructed on how to modify breathing patterns. The pacing stage may include instructions to adjust breathing rate, exhalation length, inhalation length, volume of air intake for inhalation; and/or target carbon dioxide levels. The pacing stage may be designed based on the patient's baseline data. In some cases, the second stage lasts about ten minutes or less. Following the second stage, a third stage may be used to help patients practice pacing methods. For example, the patient may attempt to maintain a breathing pattern without instructions or cues available in the second stage. In some cases, the patient may refer to biofeedback to help the patient maintain a target breathing pattern in the third stage. Biofeedback can include monitoring carbon dioxide levels and respiratory rate. In some embodiments, the third stage is a transition stage 1704 that lasts about five minutes or less. Additional details for each of the three stages are provided in the following sections.

During the baseline stage, the patient may sit quietly and breathe normally with eyes closed. Patient data may be collected to show the patient's respiration parameters prior to any instruction or modification. The patient's respiration parameters may be measured and/or recorded by a capnometer or a breathing therapy system as shown in FIGS. 1-13B and 15. Additionally, other patient parameters (e.g. oxygen saturation, blood pressure, heart rate, etc.) may be measured or monitored during the baseline stage. In some cases, the baseline stage may last two-minutes. In other embodiments, the baseline stage may be shorter or longer as needed to adequately collect the patient's pre-instruction and pre-modification parameters.

The user's information may be stored and/or electronically communicated from a capnometer to a central database or to a mobile device. In other cases, a therapist may be on-site to receive the collected data. Where the capnometer communicates the user's data to a central database or mobile device, the database or mobile device may perform an algorithm to assess an appropriate breathing therapy for the user. For example, if the user's end-tidal $CO_2$ levels are measured to be below a desired target range, the algorithm may provide instructions that the user should increase end-tidal $CO_2$ through breathing exercises. If a user has a breathing rate of 16 breaths per minute (bpm), the algorithm may provide instructions that the user should reduce breathing rate. In other embodiments, the instructions may request that the user adjust breathing rate to match a target rate.

Once the appropriate therapy is determined by the algorithm or by a therapist, the patient enters the second stage or pacing stage. In some embodiments, the pacing stage provides for visual or audio guidance to help the patient modify breathing patterns, habits, and end-tidal $CO_2$. For example, in some embodiments where a mobile device is used, the mobile device may play a set of audio tones, visual cues, pacing tones, audible instructions or music to guide the patient's cyclic rhythm of inspiration and expiration.

The audio tones may help the patient pace his breathing with target breathing patterns. For example, the audio tones may increase in volume or pitch to indicate inspiration and lower in volume or pitch to indicate expiration. Moreover, the duration of the audio tones during inspiration may be shorter than the audio tones during expiration or vice versa to indicate the length of inhalation and exhalation. In some embodiments, rising tones indicate inspirations and falling tones indicate expiration. In other embodiments, the audio tones or tone patterns include silence which indicates a pause between exhalation and inhalation or inhalation and exhalation.

Additionally, the breathing cues may guide the patient to a modified respiratory rate. Because a patient may present with a higher breathing rate to start, embodiments described provide exercises to gradually reduce breaths per minute to a target range. For example, during the baseline stage, the patient may present with 15 bpm (breaths per minute). The capnometer collects this information and communicates the data to a mobile device. The mobile device receives the user data during the baseline stage and operates an appropriate therapy protocol in the pacing stage step. The therapy protocol (or second stage) may entail a ten-minute period during which the patient breathes along with pacing or audio tones (e.g. tone patterns) to guide them in their breaths per minute.

In some embodiments, tones patterns guide the patient to adjust his breaths per minute to 13 bpm, 11 bpm, 9 bpm, or 6 bpm, etc. Although 13, 11, 9, 6 breaths per minute are given as examples, it can be appreciated that depending on a patient's baseline, modifications of the pacing tones may be required. For example, the tone pattern can be modulated to correspond to a respiration rate of 13 breaths per minute in a first therapy session and to rates of 11, 9, and 6 breaths per minute in successive sessions. However, if the patient's baseline is 13 bpm, then the treatment may begin with tone patterns for 11 bpm. In other cases, it may be desirable to use 15, 12, 10, 8, and 6 bpm patterns. In another example, the patient's breath may be below a target bpm. The tone patterns may guide the patient to increase bpm. In some embodiments the therapy guides the patient to a respiration rate of about 6 bpm to about 13 bpm.

Additionally, in some variations, the breathing cues will instruct the user to adjust volume of inhaled air to match a target volume. In some cases, the user will be instructed to reduce volume of inhaled air. The user may be taught how to breathe air such that the volume of air is at or near a target level. In some cases, reducing the volume of inhaled air can be used to treatment a disorder, condition, and/or disease. Additionally, one way to measure the volume of air in a breath is by measuring the end-tidal $CO_2$ levels.

Visual breathing guidance may be used in combination or alone for guiding the user's breathing pattern. For example, colors, lines, shapes, words, letters, pictures, etc. may be used to indicate length of inhalation or exhalation and pauses in between. Moreover, visual cues may be used to teach the user how to attain or maintain desired end-tidal $CO_2$ levels, respiratory rate, etc. For example, a graph measuring end-tidal $CO_2$ levels may be shown to encourage the user to attain or maintain a target level of end-tidal $CO_2$.

As described, instructing the user to modify breathing pattern may lead to increased end-tidal $CO_2$ levels. In some embodiments, the end-tidal $CO_2$ levels are increased or maintained at about 37 mmHg to about 43 mmHg by decreasing to or maintaining breaths per minute at about 6 bpm.

Upon completion of one or more pacing stages, the patient may enter a transition stage. The transition stage allows the patient to practice the breathing patterns used in the pacing stage without any outside guidance. However, alternatively, the pacing tones and visual/audio cues may also be provided during the transition stage depending on the patient's needs. In some cases, even where the breathing cues are provided, the patient may be instructed not to follow or rely upon the cues.

Additionally, in the transition stage, the patient may regularly or sporadically check his measured parameters including end-tidal $CO_2$ levels and respiratory rate to monitor progress. Patients may also be encouraged to attain or maintain target breathing rate and end-tidal $CO_2$ levels by monitoring measured parameters.

In some embodiments, the treatment described takes places over the course of four weeks. The three-stage exercise (baseline, pacing, and transition) may be repeated two or more times every day for multiple weeks. In some cases, the three-stage exercise is performed for one week or more, including four weeks. Each week the pacing stage may be altered based on the patient's progress. For example, if the patient has achieved a 9 bpm breathing rate, the pacing stage protocol may be changed to guide the patient to a 6 bpm breathing rate. Generally, the pacing stage will change each week. However, it can be appreciated that depending on the patient's progress, the treatment timeline may be modified accordingly. In some embodiments, the baseline duration may be about two minutes, the pacing duration about ten minutes, and the transition duration about five minutes.

In further embodiments, the tone patterns or breathing therapy may include techniques from (1) Capnometry Assisted Respiratory Therapy (CART). A therapy protocol developed by Meuret, A. E., Wilhelm, F. H. and Roth, W. T. as described in the paper "Respiratory Biofeedback-Assisted Therapy in Panic Disorder," published in Behavior Modification September 2001), issue 25, pages 584-605; (2) Targeting pCO2 in Asthma: Pilot Evaluation of a Capnometry-Assisted Breathing Training Alicia E. Meuret, Thomas Ritz, Frank H. Wilhelm, Walton T. Roth Appl Psychophysiol Biofeedback (2007) 32:99-109; and (3) the Buteyko Method which are herein incorporated by reference in their entirety.

As described, in some embodiments, the breathing therapy treatment may be executed by a system utilizing software (e.g. mobile app) that can be downloaded to a patient's personal computing device. For example, software for the therapy can be downloaded and executed on a mobile device that electronically communicates with a capnometer. The software or program may provide for immediate breathing feedback to the patient through audio guidance and visual displays, allowing the patient to adjust his or her respiration rate and end-tidal $CO_2$ levels. The software or program may store training sessions and training session results for review by a medical professional or the patient.

The program may display a graph showing the end-tidal $CO_2$ levels and breathing rate with goal lines for target values. FIG. 16 shows goal line (dashed) $CO_2$ pressure at 40 mmHg and goal line (dashed) 13 bpm for breathing rate. In some embodiments, the system may provide the patient with advice or tips during the session on how to reach goals such as raising end-tidal $CO_2$. As shown in FIG. 16, current $CO_2$ levels are indicated in a blue box that shows the $CO_2$ level of the patient's last breath. The blue line leading up to the blue box shows a record of the patient's $CO_2$ level during the current breathing session. The white box next to the Current $CO_2$ level shows the Target $CO_2$ level, which is 37-40 mmHg ("millimeters of Mercury") in the example. The number in the green box shows the current Respiration Rate (RR). The green line leading up to the green box shows a record of the patient's RR during the current breathing session. The white box next to the Current Respiration Rate shows the Target Respiration Rate.

In further embodiments, the system may alert the user if breathing rate or end-tidal $CO_2$ levels exceed a safety limit, which may include being above or below a safety limit. The system may also alert the user if the capnometer has become disconnected from the system. The graphical representation may also include icons showing the operability of the capnometer device including icons for battery use, sensor activation, and Bluetooth connectivity. The graphical representation may also include graphical user interface components for the user to manipulate (e.g. click) to receive breathing therapy instructions.

In further embodiments, the program may include a calibration protocol to prepare the device for measuring a patient's breath. In some cases, the program or software may automatically calibrate the system as described above (e.g. span and zero calibration). In other cases, the calibration software may calibrate based on ambient air in the patient's environment. Additionally, the program or software may use GPS to determine the altitude of the patient's location. Altitude may be factored into the patient's breathing therapy. For example, the calculation for $CO_2$ level may take into account barometric pressure. Altitude can be used to calculate (and get a close approximation) of barometric pressure.

Additionally, during treatment, the patient can view breathing rate, end-tidal $CO_2$ levels, or any other collected data/parameters for feedback and guidance on progress. The patient can use the display on the capnometer or on a connected mobile device to track progress. In some embodiments, the visual or audio cues for breathing pattern learning, capnometer, display, and any other components for treatment are contained in a single device. The device may include a processor for executing a pre-programmed treatment session. The processor may also electronically receive measurements from the capnometer for processing or display.

In further embodiments, the methods, systems, and devices described may be applicable to: (a) Preventative and self-directed healthcare (complies with ACA); (b) Home-based biofeedback for Panic Disorder, PTSD; (c) Assessment of asthma medication efficacy; (d) Pre hospital, triage, paramedic/EMT intubation verification; (e) Buteyko method training monitoring for asthma related self-therapy; (f) Supplemental $O_2$ home therapy-demand valve triggering for gas consumption reduction; (g) Home-based sleep studies, nasal CPAP, neonatal sleep apnea monitoring; (h) Conscious sedation procedures (outpatient surgery, colonoscopies, eye surgery, oral surgery, etc.); (i) Dental office procedures and oral surgery; (j) MRI radiology procedure monitoring—with employment non-interfering fiber optic indicator; (k) Self-controlled analgesia monitoring for pain management; and (l) Third world clinics and surgical centers.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A breathing therapy method comprising:
receiving at least a portion of a user's exhaled air in a gas inlet of a quantitative colorimetric detection system;
measuring a user's end-tidal $CO_2$ levels with the quantitative colorimetric detection system based on a color change resulting from exposure of the system to the user's exhaled air;
controlling a temperature of a colorimetric indicator in the quantitative colorimetric detection system while measuring the user's end-tidal $CO_2$ levels and
outputting a set of visual and/or audio cues from the quantitative colorimetric system with instructions for the user to adjust their breathing pattern to coincide with the cues to thereby modify the user's exhaled end-tidal $CO_2$ levels to between about 37 mmHg and 43 mmHg.

2. The method of claim 1, wherein the breathing pattern includes the exhaled $CO_2$ level and respiration rate.

3. The method of claim 1, further comprising displaying the user's measured $CO_2$ levels to provide visual feedback during treatment.

4. The method of claim 1, further comprising displaying the user's breathing rate to provide visual feedback during treatment.

5. The method of claim 1, wherein the outputting step comprises outputting a set of timed tones having an audible sequence of rising tones, falling tones, and silence.

6. The method of claim 5, wherein the rising tones indicate inspiration, falling tones indicate expiration, and silence indicates a pause in the user's respiration, the method further comprising the user breathing in at the rising tones, breathing out at the falling tones and not breathing during silent periods.

7. The method of claim 1, further comprising measuring a baseline $CO_2$ level for the user prior to modification.

8. The method of claim 1, further comprising treating post-traumatic stress disorder (PTSD), panic disorder, anxiety, asthma, hypertension, obsessive-compulsive disorder, social phobia, depression, apnea, migraines, or epilepsy by training the user to modify their exhaled $CO_2$ levels.

9. The method of claim 1, further comprising measuring a temperature of a colorimetric indicator in the quantitative colorimetric detection system while measuring the user's end-tidal $CO_2$ levels and applying a temperature correction to the measured color change.

* * * * *